US008565891B2

(12) United States Patent
Mumbru et al.

(10) Patent No.: US 8,565,891 B2
(45) Date of Patent: Oct. 22, 2013

(54) WIRELESS IMPLANTABLE MEDICAL DEVICE

(75) Inventors: Josep Mumbru, Barcelona (ES); Jordi Soler, Mataro (ES); Carles Puente, Barcelona (ES)

(73) Assignee: Fractus, S.A., Sant Cugat del Valles (ES)

( * ) Notice: Subject to any disclaimer, the term of this patent is extended or adjusted under 35 U.S.C. 154(b) by 671 days.

(21) Appl. No.: 11/921,537

(22) PCT Filed: Jun. 6, 2006

(86) PCT No.: PCT/EP2006/005368
§ 371 (c)(1),
(2), (4) Date: Feb. 8, 2008

(87) PCT Pub. No.: WO2006/131302
PCT Pub. Date: Dec. 14, 2006

(65) Prior Publication Data
US 2009/0248112 A1    Oct. 1, 2009

Related U.S. Application Data

(60) Provisional application No. 60/688,596, filed on Jun. 8, 2005.

(30) Foreign Application Priority Data

Jun. 7, 2005   (EP) .................................. 05104930

(51) Int. Cl.
*A61N 1/02*   (2006.01)
(52) U.S. Cl.
USPC .................... 607/60; 607/32; 607/33; 607/61
(58) Field of Classification Search
USPC .......................... 607/32, 33, 60, 61
See application file for complete search history.

(56) References Cited

U.S. PATENT DOCUMENTS

| 6,115,634 A | 9/2000 | Donders |
| 2003/0216793 A1 | 11/2003 | Karlsson |

(Continued)

FOREIGN PATENT DOCUMENTS

| WO | 0154225 A1 | 7/2001 |
| WO | WO-01/54225 | 7/2001 |

(Continued)

OTHER PUBLICATIONS

Hall, Antennas and Propagation for body-centric wireless communications, Artech House, 2006.

(Continued)

*Primary Examiner* — Joseph Dietrich
(74) *Attorney, Agent, or Firm* — Winstead PC

(57) ABSTRACT

One aspect of the invention relates to an implantable medical device comprising a device housing (100), at least one radio frequency circuit (104) for radio frequency communication, at least one antenna, at least one terminal to electromagnetically couple said at least one antenna to said at least one radio frequency circuit, and a dielectric compartment (101, 1661) that encompasses at least a portion of said at least one antenna. The antenna comprises a conducting pattern, at least a portion of which is shaped as a curve, wherein said curve comprises at least five segments, wherein each of said at least five segments forms an angle with each adjacent segment in said curve, wherein at least three of the at least five segments of said curve are shorter than one-fifth of the longest free-space operating wavelength of the antenna, wherein each angle between adjacent segments is less than 180°, and at least two of the angles between adjacent sections are less than approximately 115°.

67 Claims, 19 Drawing Sheets

(56) References Cited

U.S. PATENT DOCUMENTS

| | | |
|---|---|---|
| 2004/0027306 A1 | 2/2004 | Amundson |
| 2004/0176811 A1 | 9/2004 | Von Arx |
| 2004/0217916 A1 | 11/2004 | Quintero Illera |
| 2007/0279289 A1 | 12/2007 | Baliarda |

FOREIGN PATENT DOCUMENTS

| | | |
|---|---|---|
| WO | 2004025778 A1 | 3/2004 |
| WO | 2004042868 A1 | 5/2004 |
| WO | 2005087315 A1 | 9/2005 |
| WO | WO-2005/087315 | 9/2005 |

OTHER PUBLICATIONS

Smith, T. Wireless invades the medical front, Wireless Systems Design, Oct. 2003.

Ross, P.E. Managing care through the air, IEEE Spectrum, Dec. 2004.

Gosalia, K. Impedance matching and implementation of planar space-filling dipoles as intraocular implanted antennas in a retinal prosthesis, IEEE Transactions on Antennas and Propagation, Aug. 2005, vol. 53, No. 8.

Rahmant-Samii, Y. Implanted antennas for biotelemetry: antennas, safety and communications issues, IEEE Topical Conference on Wireless Communications Technology, 2003.

Christ, A. Current and future nedds for simulation of small and implanted antennas for medical applications, IEEE International Workshop on Antenna Technology Small Antennas and Novel Metamaterials, Mar. 2006.

Kim, J. et al. An implanted antenna in the spherical human head: SAR and communication link performance, IEEE Topical Conference on Wireless Communications Technology, 2003.

Kim, J. et al. Low profile antennas for implantable medical devices optimized designs for antennas/human interactions, IEEE Antennas and Propagation Society International Symposium, Jun. 2004.

Johansson, A.J., Simulation and verification of pacemaker antennas, Proceedings of the 25th annual international conference on the IEEE EMBS, Sep. 2003.

Kim, J., Implanted antennas inside a human body: simulations, designs and characterization, IEEE Transactions on Microwave Theory and Techniques, Aug. 2004.

Kim, J. Implanted antennas for medical wireless communications: characterizations, designs and performance evaluations, University of California, 2005.

Soontornpipit, P. Miniaturized biocompatible microstrip antenna using genetic algorithm, IEEE Transactions on Antennas and Propagation, 2005, vol. 53, No. 6.

Johansson, A. Wave-propagation from medical implants—influence of arm movements on the radiation pattern, 24th Annual Conference and the Annual Fall Meeting of the Biomedical Engineering Society, Engineering in Medicine and Biology, 2002.

Kwak et al. Ultra-wide band spiral shaped small antenna for the biomedical telemetry, APMC Proceedings, 2005.

Loveniers, K., International Search Report for PCT/EP2006/005368 as completed Aug. 16, 2006.

Jaggard, D.L. Expert report of Dwight L. Jaggard (redacted)—expert witness retained by Fractus. Fractus, Jan. 18, 2011.

Jaggard, D.L. Rebuttal expert report of Dr. Dwight L. Jaggard (redacted version). Fractus, Feb. 16, 2011.

Demarco, S. C. et al, Computed SAR and thermal elevation in a 0.25-mm 2-D model of the human eye and head in response to an implanted retinal stimulator—Part I: Models and Methods, IEEE Transactions on Antennas and Propagation, vol. 51, No. 9, Sep. 9, 2003.

Abdelsayed, S. M. et al, Radiation characteristics of loop antennas for biomedical implants, URSI, Sep. 2005.

Shamim, A. ; Popplewell, P.; Karam, V. et al, 5.2 GHz On-Chip antenna / inductor for short range wireless communication applications, IWAT, Mar. 6, 2006.

Yuce, M. ; Dissanayake , T. , Easy-to-swallow wireless telemetry, IEEE Microwave Magazine, Sep. 2012.

WIRELESS IMPLANTABLE MEDICAL DEVICE

CROSS-REFERENCE TO RELATED APPLICATIONS

This patent application claims the benefit of priority from U.S. Provisional Patent Application No. 60/688,596 filed Jun. 8, 2005 and European Patent Application No. EP 05104930.2 filed Jun. 7, 2005.

OBJECT AND BACKGROUND OF THE INVENTION

The present invention relates generally to novel implantable medical devices that include a new family of miniature antennas in the device. Also, the invention relates to several novel ways of arranging said miniature antennas inside implantable medical devices, and novel wireless communication systems comprising implantable medical devices with an integrated antenna.

Implantable medical devices (such as for instance cochlear implants, hearing devices, neuro-stimulators, cardioverter defibrillators, congestive heart failure devices, pacemakers, ventricular assist devices, artificial hearts, insulin pumps, drug pumps, incontinence devices, bone growth stimulators, or orthopedic implants) are currently used to treat a medical condition or pathology of a patient (e.g., an insulin pump to treat diabetes), or to overcome an impairment of a physiological functionality (e.g., a cochlear implant to restore the hearing functionality).

These devices have the capability of monitoring one or more physiological variables (such as for example cardiac heartbeat rate, blood glucose levels or blood pressure) by means of one or several sensors, and/or applying stimuli to the appropriate body organ or limb (such as for example an electrical discharge, or the release of a drug) by means of one or several actuators. Furthermore, in order to provide a particular functionality (for instance cardiac rhythm management, monitoring of activity levels, blood drug delivery or neuromuscular stimulation) the implanted medical device comprises an electronic circuitry that processes the collected physiological information and delivers the correct treatment.

Typically, an implantable medical device needs to be programmed to meet the specific particularities of the medical condition of a patient. Although this task can be performed initially either before or during the surgical procedure to implant the device into the recipient, the medical conditions or the body of the patient are likely to evolve over time, thus making it necessary to re-adjust the implanted device accordingly to these changes in order not to degrade the effectiveness of its therapeutic functionality.

The programming (including reprogramming) of the implanted medical device is usually done by controlling the device with an external programming unit. Therefore, it is advantageous to realize such programming and reprogramming using non-invasive techniques, like for example a radiofrequency link with a wireless implanted device, as it reduces discomfort to the patient and avoids the risk and the cost of surgery.

In some prior-art cases, a wireless implantable medical device and an external control unit use a near-field technique for the communication. According to this technique, signals are coupled inductively between an external antenna and an antenna in the implantable device, usually a coil antenna.

One of the problems of this technique is that, as the near-fields decay very rapidly with distance, the external antenna (typically a loop antenna) has to be placed within a few centimeters from the implanted device in order for the communication to take place, which is inconvenient for a clinician, reduces the mobility of the patient, and allows limited functionality between the implantable medical device and the external unit.

As an alternative, some prior-art implantable medical devices use far-field radiofrequency to communicate with an external unit. This option overcomes the problem of short range, as the communication can take place over greater distances, whereby this technique implies minimal restrictions on the physical activities in which a patient can participate, and enables the individual to remotely monitor and control a medical condition without feeling restricted by the medical device.

However, an important problem of this approach is the integration of an antenna in such small implantable devices, as the space required for an antenna to operate at the frequency bands typically used for medical applications is large compared to the dimensions of these devices.

Furthermore, attempts to make small antennas have resulted in these antennas being very inefficient, which leads to a decreased range, an increase in power consumption and, therefore, to shorter battery life.

The present invention addresses this problem as it discloses how to integrate an antenna in an implantable medical device such that the antenna size is compatible with the dimensions of the medical device, while exhibiting good electrical performance.

SUMMARY OF THE INVENTION

The present invention relates to devices, system and uses as defined in the corresponding independent claims. Some embodiments of the invention are defined in the dependent claims.

The present invention relates generally to novel wireless implantable medical devices that include a new family of miniature antennas in the device. Also, the invention relates to several novel ways of arranging said miniature antennas inside implantable medical devices. Some characteristic aspects of the invention are:
- The small size of the antenna, which allows the integration of the antenna in the implantable device with minimal volume overhead at typical wireless wavelengths for medical applications;
- The antenna geometry that enables such a miniaturization;
- The arrangement of the antenna in the implantable medical device.
- The compatibility of the antenna design with materials typically used for medical implants, like for example biocompatible materials.
- The wireless communication systems comprising such implantable medical devices including an antenna.

The implantable medical device of the present invention generally comprises an antenna in the form of an electrically conducting pattern integrated in the said device. One of the characteristic aspects of the invention is the geometry of said conducting pattern that facilitates the size reduction of the antenna.

In some embodiments, an antenna for an implantable medical device can be miniaturized by shaping at least a portion of the conducting trace, conducting wire or contour of a conducting sheet of the antenna (e.g., a portion of the arms of a dipole, a portion of the perimeter of the patch of a patch antenna, a portion of the slot in a slot antenna, a portion of the loop perimeter in a loop antenna, or other portions of the antenna) as a space-filling curve (SFC), as a box-counting curve, and/or as a grid dimension curve, with the antenna geometry arranged within the implantable medical device according to the present invention.

For those implantable medical devices where the size is critical and the required degree of miniaturization of the antenna is very high, the characteristic curve of the antenna can advantageously feature a box-counting dimension (and/or grid dimension) larger than approximately 1.15. For a further degree of miniaturization, the curve will be arranged such that its box-counting dimension ranges from approximately 1.5 up to approximately 3 (e.g., in the case of volumetric structures), including any subinterval of that range. For some embodiments, a curve having a box-counting dimension of about 2 is preferred.

Actually, depending on the different needs and conditions applicable to each case, the curve can have a box-counting dimension larger than a minimum value selected from the group comprising 1, 1.1, 1.2, 1.25, 1.3, 1.35, 1.4, 1.45, 1.55, 1.6, 1.65, 1.7, 1.8, and 1.9.

The curve can also have a grid dimension larger than a minimum value selected from the group comprising 1, 1.1, 1.2, 1.25, 1.3, 1.35, 1.4, 1.45, 1.55, 1.6, 1.65, 1.7, 1.8, and 1.9.

The teachings of the present invention make it possible to reduce substantially the size of an antenna so that it has little impact on the overall size of the implantable medical device in which is to be integrated. Furthermore, this application also teaches how to arrange the antenna within the implantable device so that the antenna presents good electrical performance, thus overcoming two important limitations that have complicated the commercialization of wireless fully implantable medical devices. An antenna integrated in an implantable medical device according to the present invention presents many advantages with respect to the state-of-the-art solutions.

The size reduction of the wireless implantable medical device facilitates the implantability of the device in the body of a human being or animal, as size is an important factor in determining where and how a medical device can be installed. Furthermore, a small-sized implantable device reduces the risks involved with the installation procedure, and the costs associated to more complex surgical procedures. It also offers less discomfort to the body, facilitating the acceptance after installation.

The good electrical performance of the antenna integrated in a wireless implantable medical device, improves the ability of the implanted device to communicate with an external unit (such as, for instance and without limitation, a controller). As a consequence, the implantable device exhibits an enhanced adaptability over time in front of changes in the medical condition of the patient, or changes in the body that affect the way the device senses and/or interacts with it. Such an implantable device has the flexibility to react to these changes and modify the way it performs its tasks. An external programming unit can reprogram the controlling algorithms (such as for instance, the pacing mode for a pacemaker, or the drug dosage for a drug infusion pump) via a wireless link. The adaptability feature of the wireless implantable medical device ensures that the device will deliver a therapy appropriate to the changing medical conditions of the patient, thus extending the useful life of the device.

Furthermore, a good electrical performance of an antenna integrated in an implantable medical device is desirable to reduce power consumption and extend battery life, which translates into decreasing the frequency with which patients need to undergo surgery to have a battery replaced.

In some bands of operation of the wireless implantable medical device, the ohmic-losses of the body tissues can be particularly high, which can result in a significant degradation of the electrical parameters (such as, for instance but not limited to, efficiency, gain, radiation pattern, bandwidth, and/or impedance level) of the antenna integrated in the wireless implantable medical device of the present invention.

Therefore, in certain cases, it can be advantageous to provide insulation between an antenna integrated in the wireless implantable medical device and the body tissues surrounding said device. In general it will be advantageous to insulate from the body tissues with high ohmic losses those parts of the antenna and/or the implantable medical device in which the surface currents induced by the operation of the antenna are strong.

In some embodiments, insulation is obtained by creating a cavity within the dielectric compartment (such as a plastic header) that encompasses at least a portion of the antenna. The said cavity can encompass partially or completely said at least a portion of the antenna that is located within the dielectric compartment. In some cases, the cavity can be substantially empty (i.e., vacuum is created in it) while in other cases the cavity can be partially or completely filled with a biocompatible material with low dielectric losses and/or low dielectric constant.

In some other embodiments, enhanced insulation between the wireless implantable medical device and the surrounding body tissues can be obtained by partially or totally coating the region of the device containing the antenna with a layer of biocompatible dielectric material with low losses and/or low dielectric constant. In some cases, the device housing itself will be partially or completely coated with a biocompatible dielectric material with low dielectric losses and/or low dielectric constant. Coating at least a portion of the wireless implantable medical device with a layer of biocompatible dielectric material with low dielectric losses and/or low dielectric constant is in some cases preferable to creating a cavity within the dielectric compartment of the device due to its lower mechanical complexity.

In some examples, the thickness of the coating layer of biocompatible material with low dielectric losses and/or low dielectric constant can be 1 mm, 2 mm, 3 mm, 4 mm, 5 mm, 6 mm, 8 mm, 10 mm or even larger.

Plastic materials and dielectrics typically used for implantable medical devices comprise for instance, and without limitation, thermoplastic urethane (tecothane), polytetrafluoroethylene (PFTE), expanded polytetrafluoroethylene (EFTE) and polyetheretherketone (PEEK). In some embodiments, it will be preferable to use dielectric materials with low dissipation factor (loss tangent or dielectric losses) at least in a portion of the implantable device, in the proximity of the antenna.

In the present text, low dielectric losses imply a dissipation factor smaller than approximately $10^{-2}$, or $5\times10^{-3}$, or $10^{-3}$, or $5\times10^{-4}$, or even $10^{-4}$ for at least one of operating frequencies of the antenna.

In some cases biocompatible dielectric materials with low dielectric constant will be preferred. In the present text, the low dielectric constant implies a dielectric constant smaller than a maximum value selected from the group including 4.0, 3.8, 3.6, 3.4, 3.2, 3.0, 2.8, 2.6, 2.4, 2.2, 2.0, 1.8, 1.6, 1.4 and 1.2.

Biocompatible dielectric materials used for the wireless implantable medical device of the present invention can be permeable or impermeable. In some embodiments those parts of the wireless implantable medical device made of dielectric material that are in contact with the antenna will preferably be impermeable.

Another aspect of the invention relates to radiofrequency communication systems comprising an implantable medical device with an antenna according to the present invention, such as for example a novel medical remote monitoring system comprising these new wireless implantable devices.

BRIEF DESCRIPTION OF THE DRAWINGS

Further characteristics and advantages of the invention will become apparent in view of the detailed description which follows of a set of preferred embodiments of the invention, given for purposes of illustration only and in no way meant as a definition of the limits of the invention, and made with reference to the accompanying drawings, in which.

DESCRIPTION OF THE PREFERRED EMBODIMENTS

Figure 1:
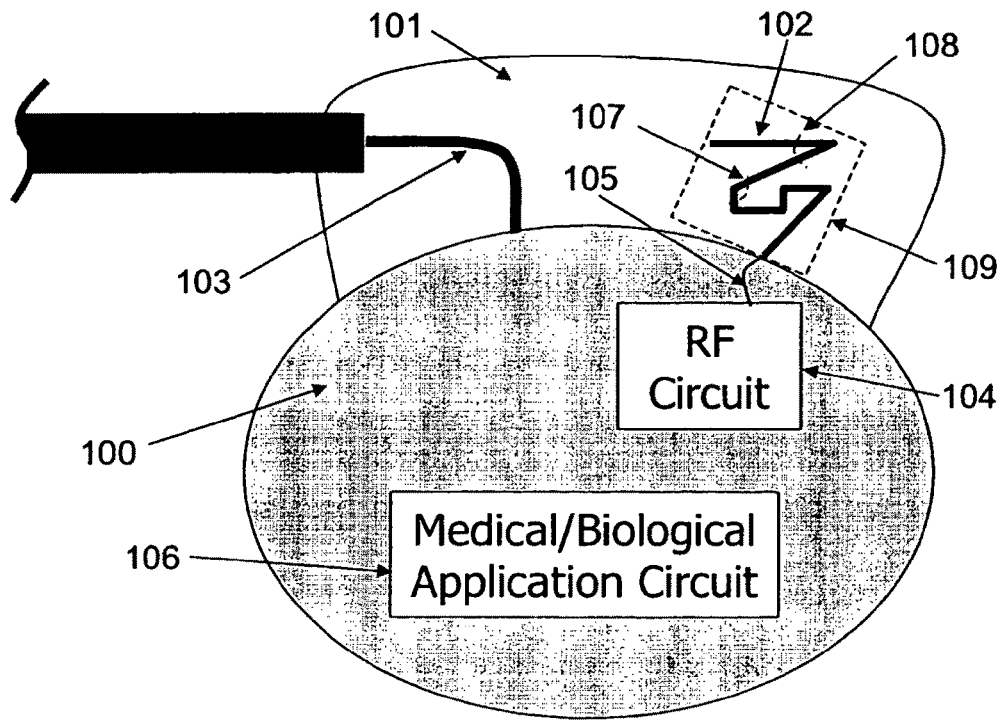
FIG. 1—Embodiment of an implantable medical device including an antenna formed from a conducting pattern having seven segments according to the present invention.

In accordance with some embodiments of the invention, the implantable medical device comprises: a device housing, a radio frequency (RF) circuit, an electronic circuit that provides a medical or biological function (such as for instance cardiac rhythm management in the case of a pacemaker), a power source (such as a battery), an antenna, a dielectric compartment (such as for instance a plastic header) that encompasses at least a portion of the antenna, and at least one terminal to electromagnetically couple the antenna to the RF circuit. The housing of the device is usually made of a biocompatible metal or alloy (such as for instance titanium), which has the property of shielding the inside electronics from the outside radiations. In some embodiments, the housing can also implement other functions, or have different uses, such as for example an electrode to deliver electrical pulses, or discharges. In some preferred embodiments, the antenna comprises a conducting pattern, at least a portion of which includes a curve shaped as a geometry chosen from the following set: space-filling curve (SFC), box-counting curve, or grid dimension curve.

In the context of this application, a space-filling curve (SFC) is defined as a curve comprising at least five segments or sections, each of the at least five segments or sections forming an angle or bend with each adjacent segment or section in the curve, at least three of the segments being shorter than one-fifth of the longest free-space operating wavelength of the antenna. Each angle between adjacent segments is less than 180° (i.e., no pair of sections or segments define a longer straight segment) and at least two of the angles between adjacent sections are less than approximately 115°.

The angles or bends between adjacent segments or sections increase the degree of convolution of the SFC leading to a curve that is geometrically rich in at least one of edges, angles, corners or discontinuities, when considered at different levels of detail.

A space-filling curve can be fitted over a flat or curved surface, and due to the angles between segments, the physical length of the curve is larger than that of any straight line that can be fitted in the same area (surface) as the space-filling curve. Additionally, to shape the structure of a miniature antenna, a majority of the segments of an SFC should be shorter than at least one fifth of the longest free-space operating wavelength, and possibly shorter than one tenth of the longest free-space operating wavelength. The space-filling curve should include at least five segments in order to provide some antenna size reduction, however a larger number of segments may be used (such as for instance 10, 15, 20, 25 or more segments). In general, the larger the number of segments, and the narrower the angles between them, the smaller the size of the final antenna.

An antenna shaped as a SFC is small enough to fit within a radian sphere (e.g., a sphere with a radius equal to the longest free-space operating wavelength of the antenna divided by 2π). However, the antenna features a resonance frequency lower than that of a straight line antenna substantially similar in size.

In some embodiments, the said conducting pattern of the antenna comprises straight segments, while in other embodiments the said conducting pattern comprises curved segments. Additionally, in some cases the curve is arranged such that at least two of the angles are defined respectively in the clockwise and counter-clockwise directions at opposite sides of the curve to minimize the inductive coiling effect.

In certain embodiments of the present invention, the antenna integrated in the implantable medical device will be such that at least a portion of the curve comprised in the conducting pattern of the said antenna includes an arrangement of its segments that is self-similar with respect to the entire curve. In some embodiments, at least a portion of the conducting trace, conducting wire or contour of a conducting sheet of the antenna included in the implantable medical device will be advantageously shaped as a curve selected from the group consisting essentially of Hilbert, Peano, SZ, ZZ, HilbertZZ, Peanoinc, Peanodec, and PeanoZZ (cf. WO-A01/54225 which describes these curves and which is incorporated herein by reference). In other embodiments, the arrangement of the segments defining the SFC portion of the antenna geometry will be dissimilar with respect to the entire curve, that is such an arrangement will be not self-similar with respect to the entire curve.

One aspect of the present invention is the box-counting dimension, or grid dimension, of the curve that defines at least a portion of the antenna. For a given geometry lying on a surface, the box-counting dimension, or grid dimension, is computed in the following way: first a grid (such as a grid with 25 boxes) with boxes of size L1 is placed over the geometry of the curve, such that the grid covers completely the whole said geometry, and the number of boxes N1 that include at least a point of the geometry is counted. Secondly, a grid with boxes of size L2 (L2 being smaller than L1) is also placed over the geometry, such that the grid completely covers the geometry, and the number of boxes N2 that include at least a point of the geometry is counted again. The box-counting dimension, or grid dimension, D is then computed as:

$$D = -\frac{\log(N2) - \log(N1)}{\log(L2) - \log(L1)}$$

In terms of the present invention, the box-counting dimension, or grid dimension, is computed by placing the first and second grids inside the minimum rectangular area enclosing the curve of the antenna and applying the above algorithm.

The first grid could be chosen such that the rectangular area is meshed in an array of at least 5×5 boxes or cells, and the second grid can then be chosen such that L2=½L and such that the second grid includes at least 10×10 boxes (for calculating the box-counting dimension, grids are taken that comprise n×n boxes, that is, the number of columns equals the number of rows; contrarily, as understood from FIGS. 20-23, for calculating the grid dimension, the grid has n×m boxes, n≠m, that is, the grid has a number of rows that differs from the number of columns of the grid; when calculating the grid dimension, the minimum number of boxes of the first grid should preferably be 25, and the second grid should preferably comprise at least 100 boxes). By the minimum rectangular area it will be understood such area wherein there is not an entire row or column on the perimeter of the grid that does not contain any piece of the curve. Thus, some of the embodiments of the present invention will feature a box-counting dimension larger than one, some other embodiments will have a box-counting dimension larger than approximately 1.15, and in those applications where the required degree of miniaturization is higher, the designs will feature a box-counting dimension ranging from approximately 1.5 up to approximately 3, with any subinterval within this range included. For some embodiments, a curve having a box-counting dimension of about 2 is preferred. The same applies to the grid dimension of the curve.

For very small antennas, that fit for example in a rectangle of maximum size equal to one-twentieth of the longest free-space operating wavelength of the antenna, the box-counting dimension will be necessarily computed with a finer grid. In those cases, the first grid will be taken as a mesh of 10×10 equal cells, while the second grid will be taken as a mesh of 20×20 equal cells, and then D is computed according to the equation above. In the cases of small implantable medical devices in which the antenna is to be arranged according to a planar design, it is preferred that the dimension of the curve included in the antenna geometry have a value close to D=2.

In general, for a given resonant frequency of the antenna, the larger the box-counting dimension of the curve, the higher the degree of miniaturization that will be achieved by the antenna. One way of enhancing the miniaturization capabilities of the antenna according to the present invention is to arrange the several segments of the curve of the antenna pattern in such a way that the curve intersects at least one point of at least 14 boxes of the first grid with 5×5 boxes or cells enclosing the curve. Also, in other embodiments where a high degree of miniaturization is required, the curve crosses at least one of the boxes twice within the 5×5 grid, that is, the curve includes two non-adjacent portions inside at least one of the cells or boxes of the grid.

Figure 19:
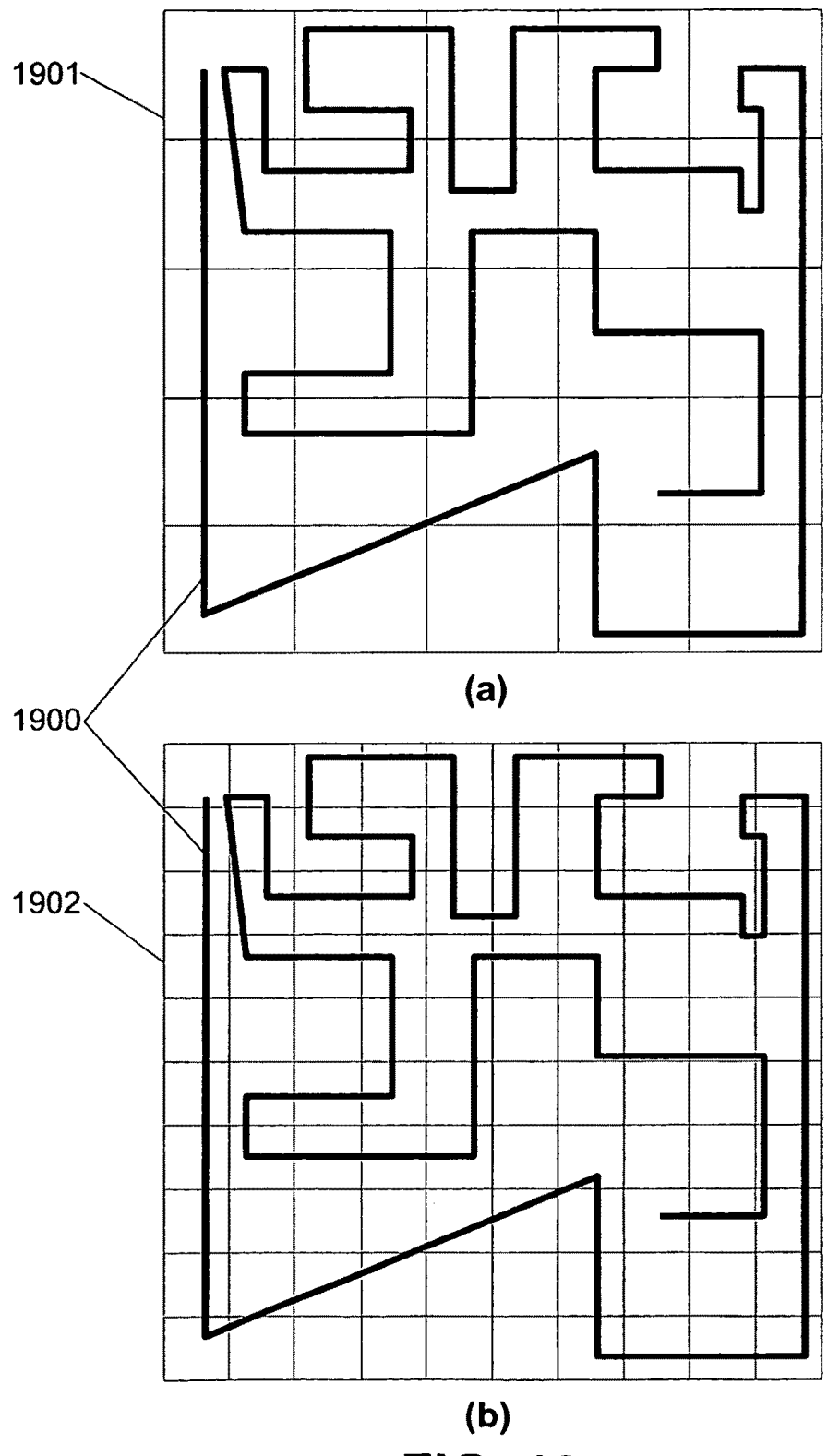
FIG. 19—Example of a box counting curve located in a first grid of 5×5 boxes and in a second grid of 10×10 boxes.
Figure 20:
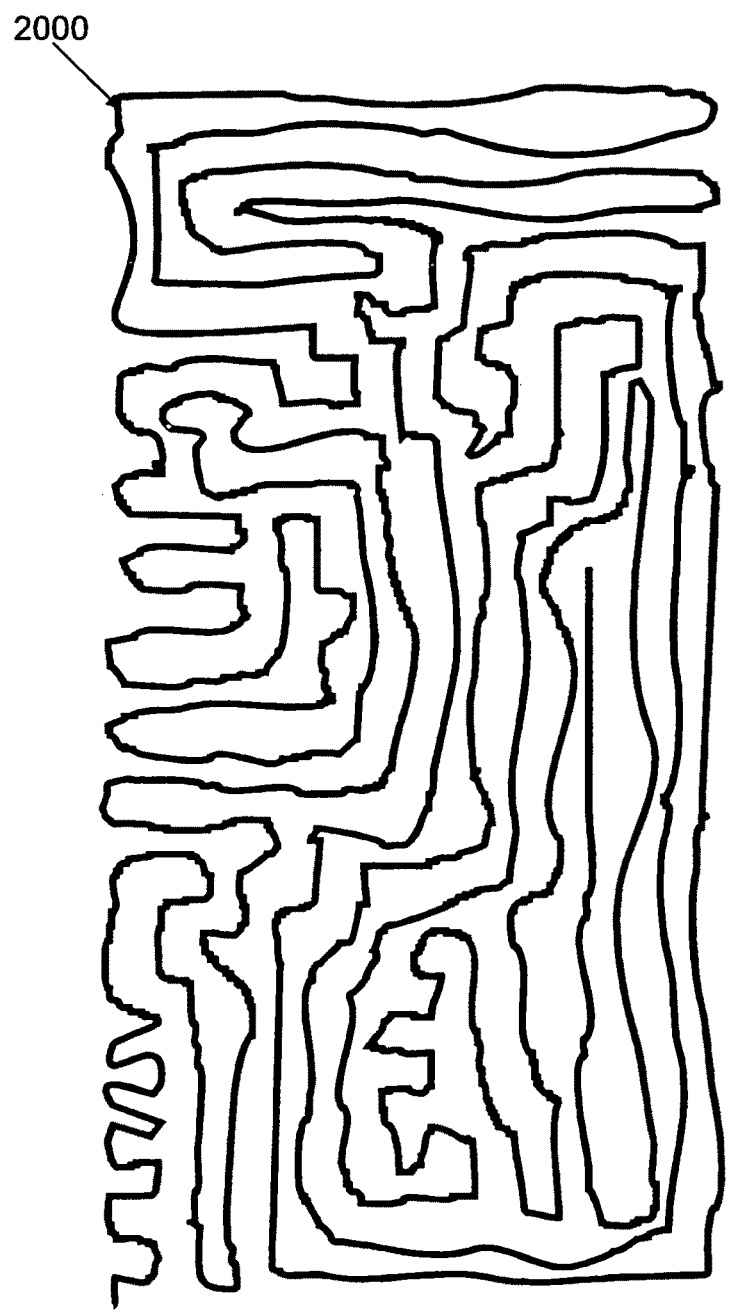
FIG. 20—Example of a grid dimension curve.
Figure 21:
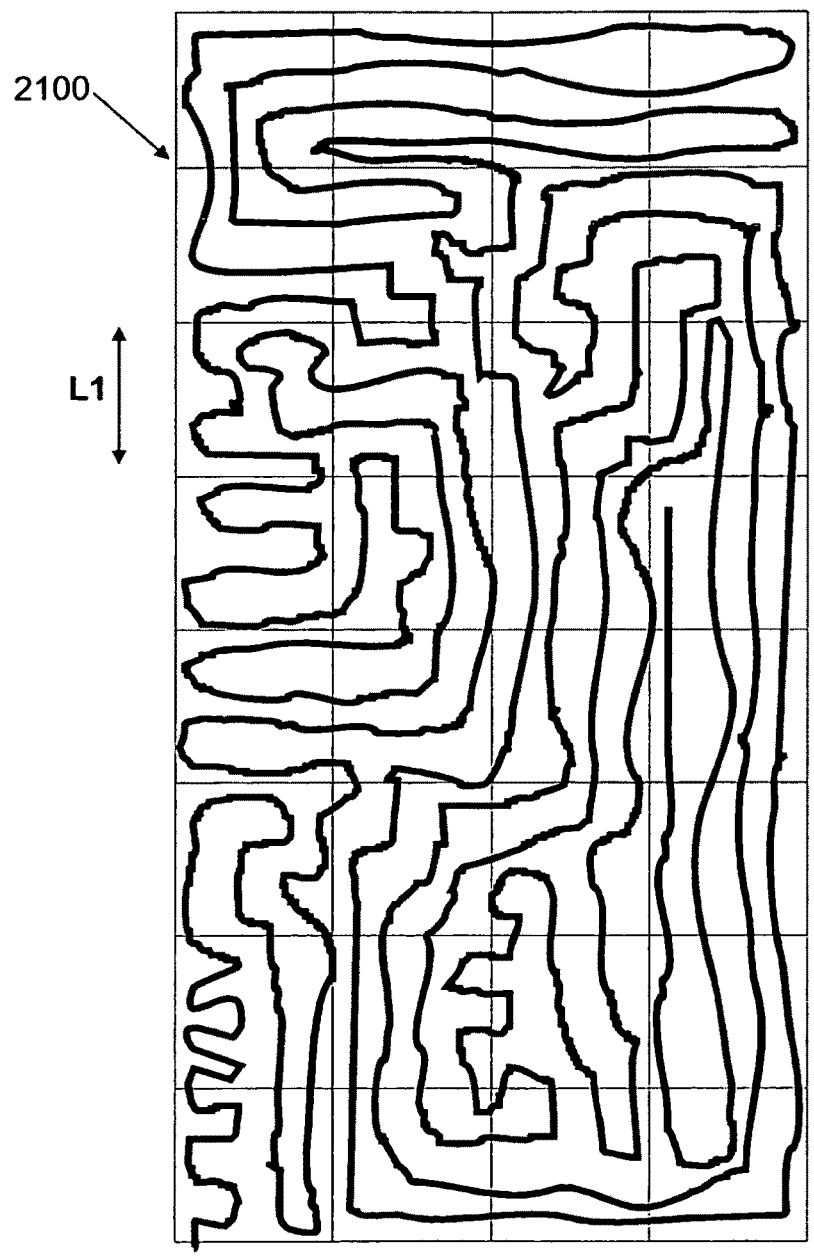
FIG. 21—Example of a grid dimension curve located in a first grid.
Figure 22:
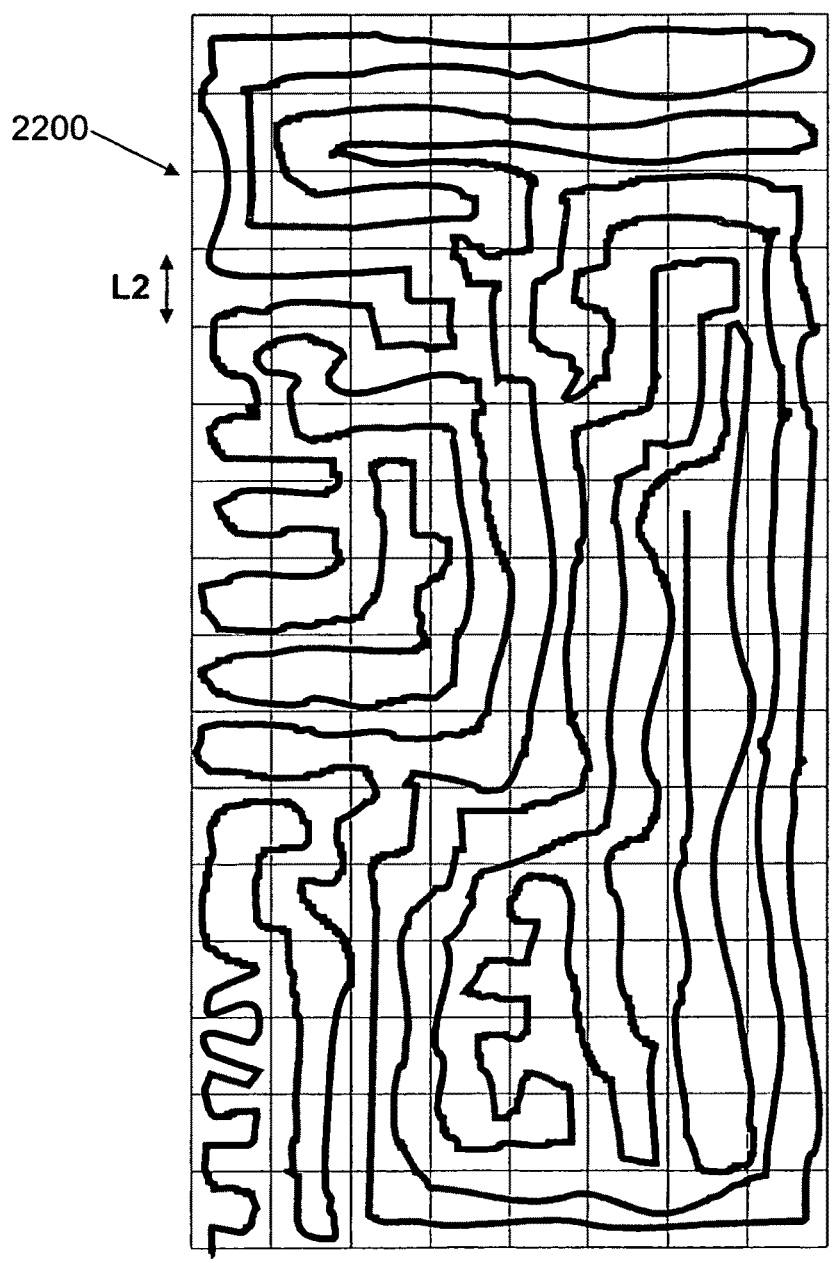
FIG. 22—Example of a grid dimension curve located in a second grid.
Figure 23:
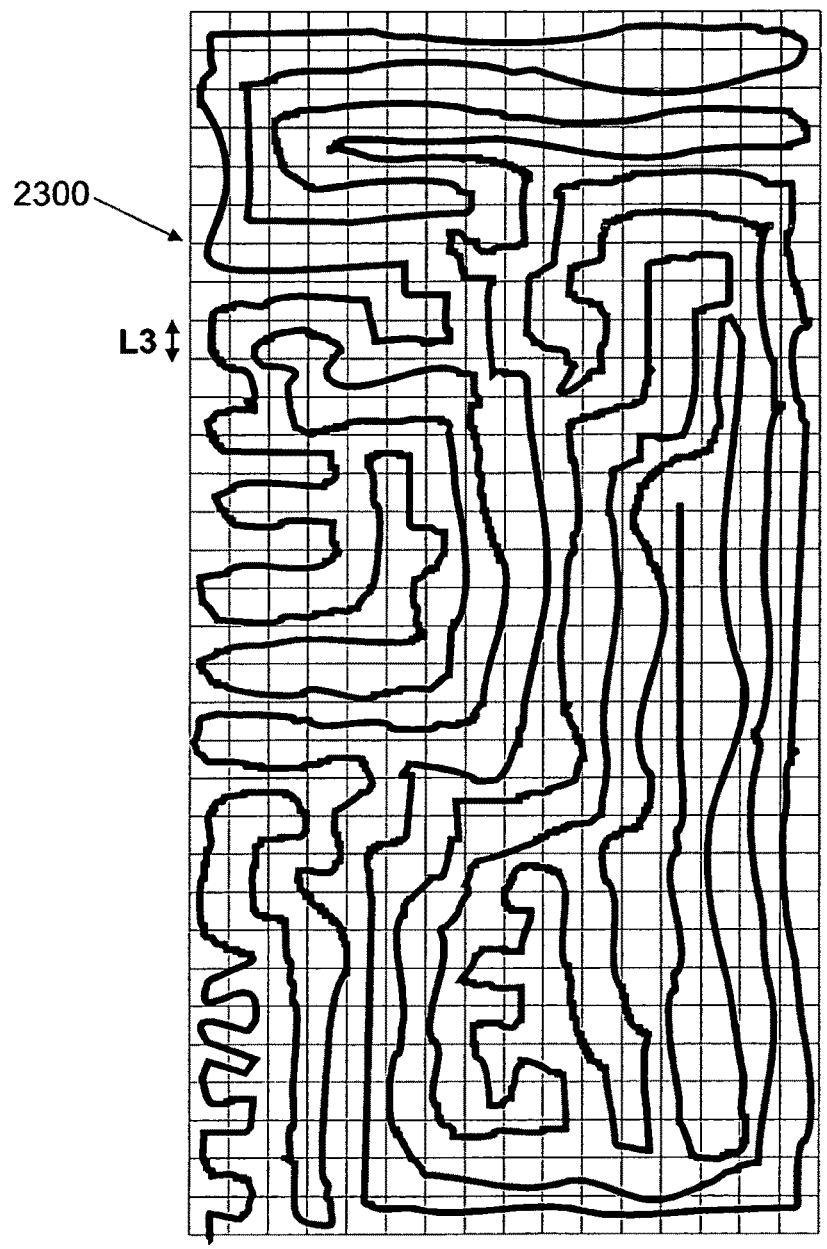
FIG. 23—Example of a grid dimension curve located in a third grid.

An example of how the box-counting dimension is computed according to the present invention is shown in FIGS. 19a and 19b. An example of a dissimilar, non-self-similar curve (1900) according to the present invention is placed under a 5×5 grid (1901) and under a 10×10 grid (1902). As seen in the graph, the curve (1900) touches N1=25 boxes in grid (1901) while it touches N2=78 boxes in grid (1902). In this case the size of the boxes in grid (1901) is twice the size of the boxes in (1902). By applying the equation above it is found that the box-counting dimension of curve (1900) is, according to the present invention, equal to D=1.6415. This example also meets some other characteristic aspects of some preferred embodiments within the present invention. The curve (1900) crosses more than 14 of the 25 boxes in grid (1901), and also the curve crosses at least one box twice, that is, at least one box contains two non-adjacent segments of the curve. In fact, (1900) is an example where such a double crossing occurs in 13 boxes out of the 25 in (1901).

It is noted that, according to the present invention, the antenna structure is not limited to a planar structure. In the case of non-planar, multi-layer or volumetric structures for the antenna pattern within an implantable medical device, the box-counting algorithm can be computed by means of a three-dimensional grid, using parallelepipeds as cells instead of rectangles, and meshes with 5×5×5 cells and 10×10×10 or 20×20×20 cells respectively. In those cases, such a curve can have a box-counting or grid dimension larger than D=2 and, in some cases, up to D=3.

For the purposes of this patent document, curves in which at least a portion of the geometry of the curve has a box-counting dimension, or grid dimension, larger than 1 are referred to as box-counting curves, or grid-dimension curves.

The present invention applies to several antenna topologies, both balanced and unbalanced. In particular, monopoles, dipoles, loops, folded and loaded monopoles and dipoles and their slot or aperture equivalents (slot monopoles, slot dipoles, slot loops, folded and loaded slot monopoles and dipoles) are some of the structures that can be arranged according to the present invention. Other structures include shorted and bent monopoles (L monopoles, IFA), multi-branch structures, coupled monopoles and dipole antennas and their aperture equivalents. All of them would include the characteristic pattern built on a component of the implantable medical device according to the present invention.

Another possible antenna configuration is a microstrip or patch antenna, including their shorted versions (shorted patches and planar inverted-F or PIFA structures); nevertheless for the planar cases a particular selection of the disclosed geometries could be considered to achieve the required degree of miniaturization. In particular, the characteristic pattern of the invention could include at least a curve with fourteen (14) segments, with at least six (6) of the segments being shorter than one-twentieth of the longest free-space operating wavelength of the antenna. The rest of the general conditions that conform the essential geometric aspects of the invention, as described above, apply to the microstrip patch and their shorted versions as well.

In those embodiments in which the antenna is unbalanced, the antenna may require of a radiofrequency (RF) ground plane or counterpoise. In some cases, the RF ground plane can be coupled, either through direct contact or electromagnetic coupling, to the conductive housing of the device. In other embodiments, the RF ground plane or counterpoise may be internal to the metal housing of the device and insulated from said metal housing.

Another aspect of the present invention relates to the arrangement of the antenna inside the medical device that is implanted in the body of a human being or animal.

In some embodiments it will be advantageous to integrate the antenna directly on the metal housing of the implantable device. For example, a slot or an aperture could be created in the housing of the device to obtain a slot antenna or an aperture antenna. Although this approach can degrade the effectiveness of the shielding of the metal housing, such a solution would allow to integrate the antenna in the device with minimal increase in the size of the device. Whenever necessary to seal the implantable device so that bodily fluids stay outside the housing, at least the portion of the implantable device containing the antenna could be covered with a layer or film of a dielectric material.

In some embodiments, the implantable medical device comprises, or is connected to, one or more electrodes that are applied on the appropriate parts of the body to either sense the electrical activity of a physiological signal, and/or to deliver electrical stimuli. The electrodes usually have a metal lead at the end that is to be connected to the electronic circuit inside the housing of the device, and such a connection is implemented by means of feedthroughs. To guarantee the impermeability inside the housing of the implantable device, the region containing feedthroughs and electrode leads is usually encompassed by biocompatible plastic material (such as for instance thermoplastic urethane, also known as tecothane) forming a header.

As an alternative to the integration on the housing, an antenna according to the present invention can be integrated within the plastic header of the implantable medical device. In some cases, this approach can be advantageous as:

No additional compartment is necessary for the antenna. The antenna shares the same compartment as the one required for the electrode leads of the device.

All feedthroughs (those for the electrode leads, and those for feeding the antenna) are concentrated in one region on the housing of the implantable medical device.

The antenna can be placed further away from the device housing, thereby enhancing the radioelectric performance of the antenna (such as for example antenna bandwidth or radiation efficiency), without impacting on the overall size of the implantable device.

FIG. 1 shows one embodiment according to the present invention. The implantable medical device comprises a metallic housing (100) and a plastic header (101). One or more therapy-leads, such as for instance an electrode lead like the one labeled as (103), come out from the housing (100) by means of feedthroughs into the region that is covered by the header (101). The antenna (102) is arranged inside the header (101) of the implantable device. Although in some embodiments the implantable medical device will have electrode leads or therapy leads coming out the device (for instance through the header of the device), in other embodiments the implantable medical device will not come with such therapy leads. In such embodiments, the implantable device can instead have some electrode lead receptacles, into which the electrode leads can be plugged in. Moreover, in some other embodiments the device might not even need any electrode or therapy leads for its functioning. According to the present invention, a majority of the segments that form the antenna (102) can be shorter than one fifth of the longest operating wavelength, and the antenna can fit in a rectangular area (109) with a maximum side length that is smaller than the longest operating wavelength for the antenna divided by five.

The particular embodiment illustrated in FIG. 1 includes a monopole antenna with a single radiating arm. The arm is formed by five or more segments (seven segments in this particular example) with at least two angles such as (107) and (108) being less than 115°. Although not required, it is preferred that at least two of the angles that are less than 180° degrees are defined in the clock-wise and counter clock-wise directions at the opposite sides of the curve: right side for (107) and left for (108). The antenna (102) is connected by means of a conductor (105), such as for instance a feedthrough, to an RF circuit (104) internal to the housing (100).

The monopole antenna is an unbalanced, asymmetrical structure, which requires that at least one terminal of the RF circuit (104) be connected to a ground plane. The metallic housing (100) can be optionally connected to the RF ground plane, either at RF frequencies, or at low frequencies including DC, or both.

In some embodiments, it is preferred that the antenna (102) is arranged substantially perpendicular to the contact surface between the metallic housing (100) and the header (101), because such an arrangement reduces the size of the projection of the rectangle (109) or parallelepiped in which the antenna (102) can be circumscribed on the metallic housing (100) of the implantable device. By reducing such a footprint on such a metallic housing, the capacitive coupling to said housing is reduced, improving the antenna performance in terms of efficiency, the voltage standing wave ratio (VSWR), the bandwidth or a combination of one or more of those effects.

Figure 13:
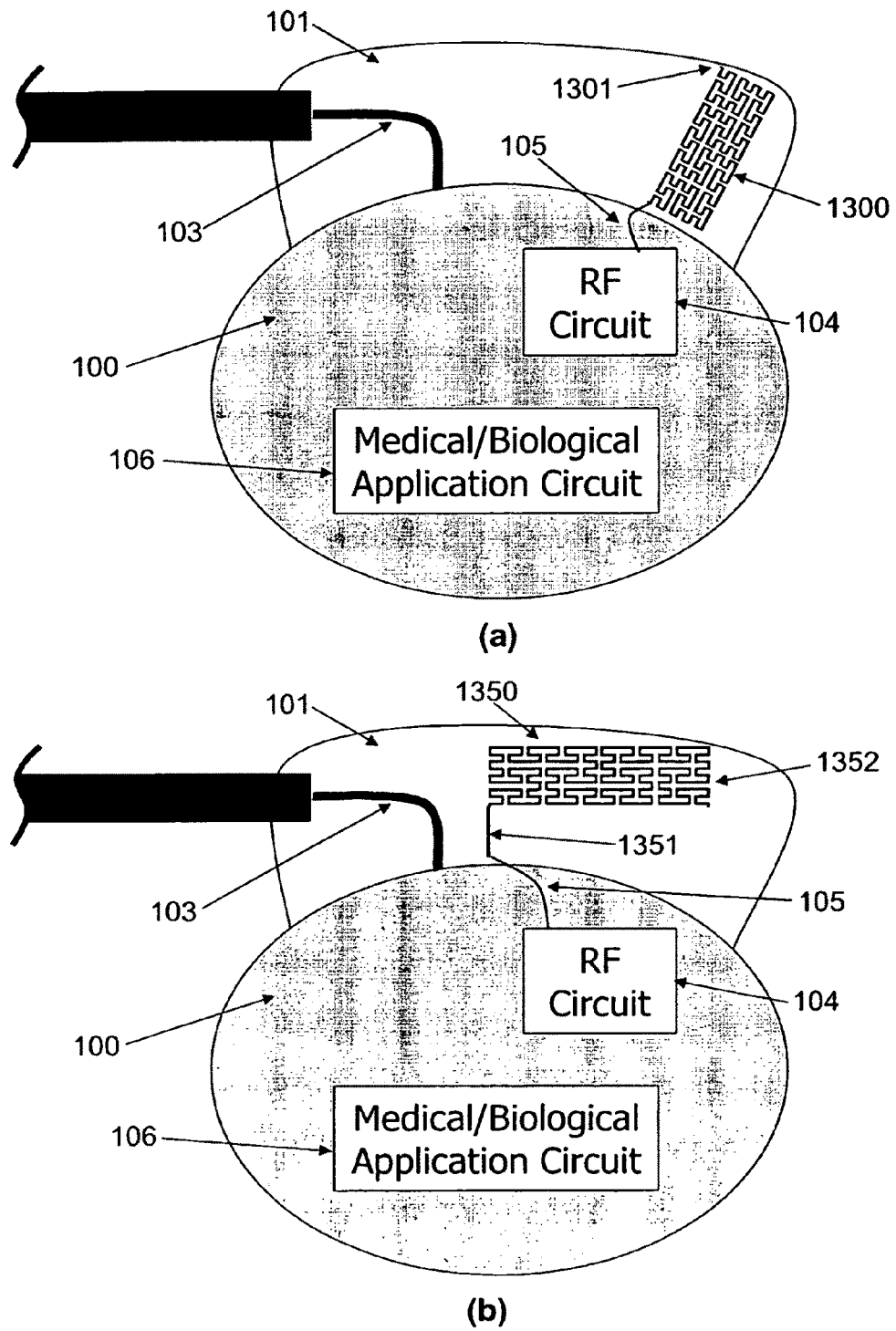
FIG. 13—Embodiments of an implantable medical device including a monopole antenna according to the present invention integrated within the header of the implantable device.

FIG. 13 shows some embodiments in which the antenna is integrated in the header (101) of the device. In FIG. 13a, it is advantageous for the antenna (1300) to protrude from the metallic housing (100) as much as permitted by the physical dimensions of the header (101). Additionally, in some cases in which the antenna (1300) comprises a conducting wire, as in the case of monopole antennas, for example, it is preferred that the end of the said conducting wire that is not used to feed the antenna (1301) be placed as far as possible from the housing of the device to improve the antenna performance.

In some other embodiments (as for example in FIG. 13b), it is preferred to arrange the antenna (1350) within the header (101) of the device in such a way that the geometry of the antenna (1350) comprises a first portion (1351) that protrudes from the housing (100) of the device, and a second portion (1352) substantially perpendicular to the said first portion (1351) of the antenna (1350). In some cases, said second portion (1352) of the antenna (1350) will be arranged substantially perpendicular to the contact surface between the metallic housing (100) and the header (101) to minimize the projection of said second portion (1352) of the antenna (1350) on the housing (101) of the device. In some other cases, said second portion (1352) of the antenna (1350) will be arranged substantially parallel to the contact surface between the metallic housing (100) and the header (101), so that the distance between said second portion (1352) of the antenna (1350) and the housing (100) of the device is maximized.

An alternative embodiment to the one including a monopole in FIG. 1 could, instead, include a folded monopole. In order to arrange the antenna (102) within the header (101) of the implantable device as a folded monopole, the free end of the monopole can be connected by means of a conductor to a grounding terminal of the RF circuit (104).

Figure 2:
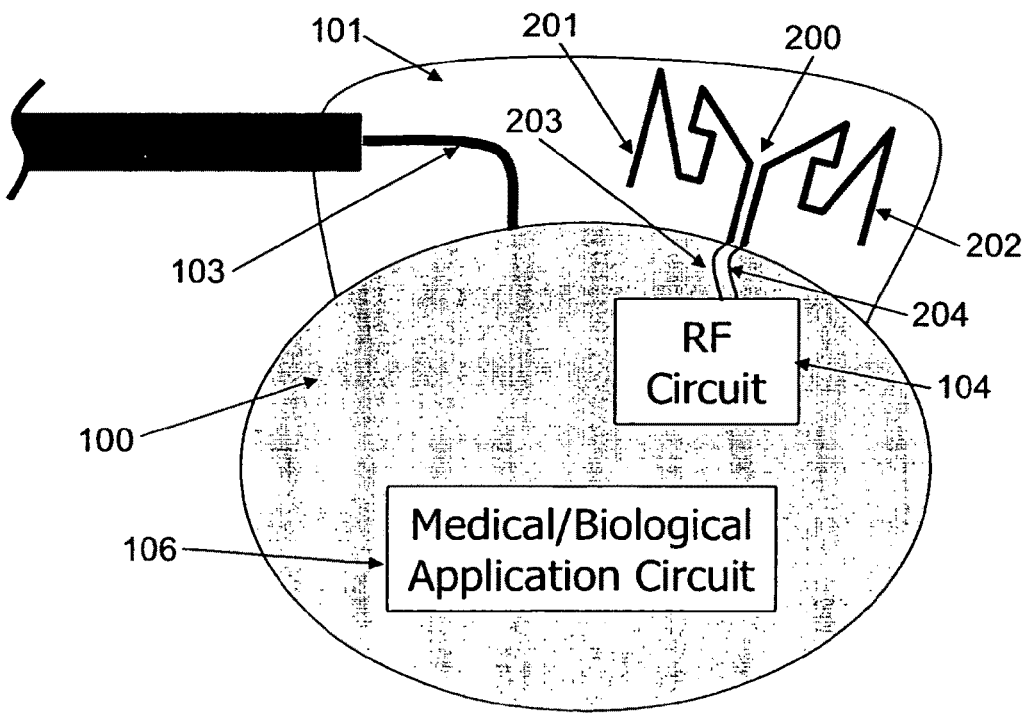
FIG. 2—Embodiment of an implantable medical device including a dipole antenna according to the present invention.

FIG. 2 shows another embodiment of the present invention where the implantable medical device includes a dipole antenna (200) according to the present invention. Such a dipole antenna has two radiating arms (201) and (202) and is excited in a differential mode by connecting the antenna (200) to a RF circuit (104) by means of a couple of conductors (203) and (204) placed one close to the other, such as for instance two feedthroughs. The use of a differential antenna, such as a dipole in this particular embodiment, is advantageous to obtain an electrical performance of the antenna that is substantially independent of the RF ground plane of the implantable medical device. Also, in some particular arrangements of the RF circuit, a need for a balun element can be eliminated or reduced. However, a differential feeding scheme requires additional feedthroughs to excite the antenna, and as much as approximately twice the space within the header to arrange the conducting trace or wire of the antenna, when compared to a monopole antenna. In some embodiments, it can be advantageous to use, in the implantable medical device, a folded dipole antenna (as shown for example in FIGS. 16c and 16d), wherein at least a portion of the conducting trace of the antenna is shaped as a curve according to the present invention. Such an antenna configuration makes it possible to increase the antenna input impedance and/or the radiation bandwidth.

Figure 3:
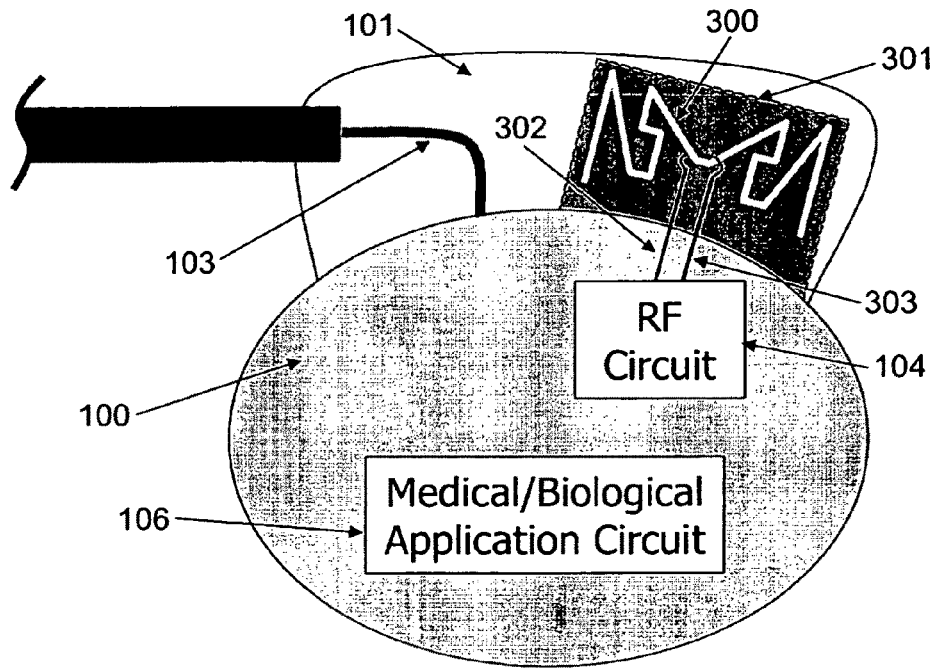
FIG. 3—Embodiment of an implantable medical device including a slot or aperture antenna according to the present invention.

FIG. 3 shows an embodiment of the present invention that includes a slot or aperture antenna in the implantable medical device. The slot comprises a gap or slit (300) that is formed on a conducting pattern (301) within the header (101). In some embodiments, the unfolded length of said gap will be substantially close to a half of an operating wavelength inside the living body, or a multiple of it, to enable resonance. The conducting pattern (301) is arranged substantially orthogonal to the contact surface between the metallic housing (100) and the header (101) of the implantable device. Optionally, this conducting pattern (301) can be grounded to an RF ground plane of the implantable medical device. To feed the slot antenna, two conducting terminals (302) and (303) connect the antenna, for instance by means of two feedthroughs, with an RF circuit (104) internal to the metallic housing (100) of the device. The two conducting terminals (302) and (303) will be placed at opposite sides of the curve forming the slot. In some embodiments, said feeding points will be substantially close to the middle point of the slot, while in other embodiments the two feeding terminals will be closer to one of the at least two ends of the slot.

Figure 4:
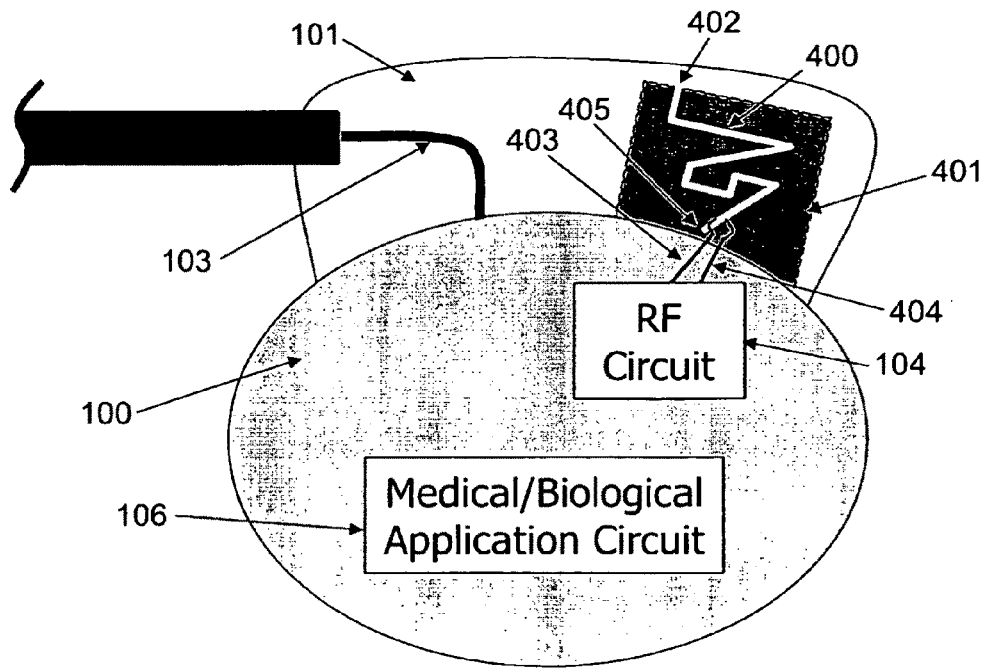
FIG. 4—Embodiment of an implantable medical device including a slot or aperture antenna according to the present invention.

Another example of embodiment comprising a slot antenna is disclosed in FIG. 4. In this particular case, the slot (400) features an open end (402). That is, the slot (400) intersects the perimeter of the conducting substrate in which the slot is located (401) in at least one point (402). In other words the slot (400) is not completely surrounded by conducting material (contrarily to what is shown in FIG. 3). In some preferred embodiments, the unfolded length of such a slot intersecting the perimeter of the conducting surface will be substantially close to a quarter of an operating in-body wavelength, or an odd multiple of it. This will allow the antenna to resonate and therefore to maximize radiation efficiency, bandwidth and link range while keeping the size of the implantable medical device small. As in the embodiment shown in FIG. 3, the slot (400) is fed at the two opposite sides of the curve by means of two terminal conductors (403) and (404). In some applications, the slot antenna embodiment is preferred over the monopole or dipole arrangements shown in FIGS. 1 and 2 respectively because radiation efficiency is quite higher (current flows all over the pattern and not necessarily only along the curve). Also, the impedance can be controlled by moving the feeding terminals (403) and (404) to different points along the antenna perimeter. In some embodiments, the terminals will be preferably close to the short-end (405) of the slot, while in others the terminals will be substantially close to the middle point of the slot, and yet in some other embodiments the two feeding terminals might be closer to the open end of the slot.

Other means to excite the slots (300) or (400) are also possible within the scope of the present invention, such as for instance using just one feeder at one side of the slot and a ground at the opposite side, using a transmission line coupled to the slot, such as for instance microstrip line, a strip-line, a slot line or a co-planar line crossing over or coupled to the slot.

A slot antenna can also be implemented by means of at least one slot in the metallic housing 100, in which case said slot can be covered by some kind of insulator or coating arranged to make the device impermeable and/or to insulate it from the surrounding tissues and/or fluids.

Figure 5:
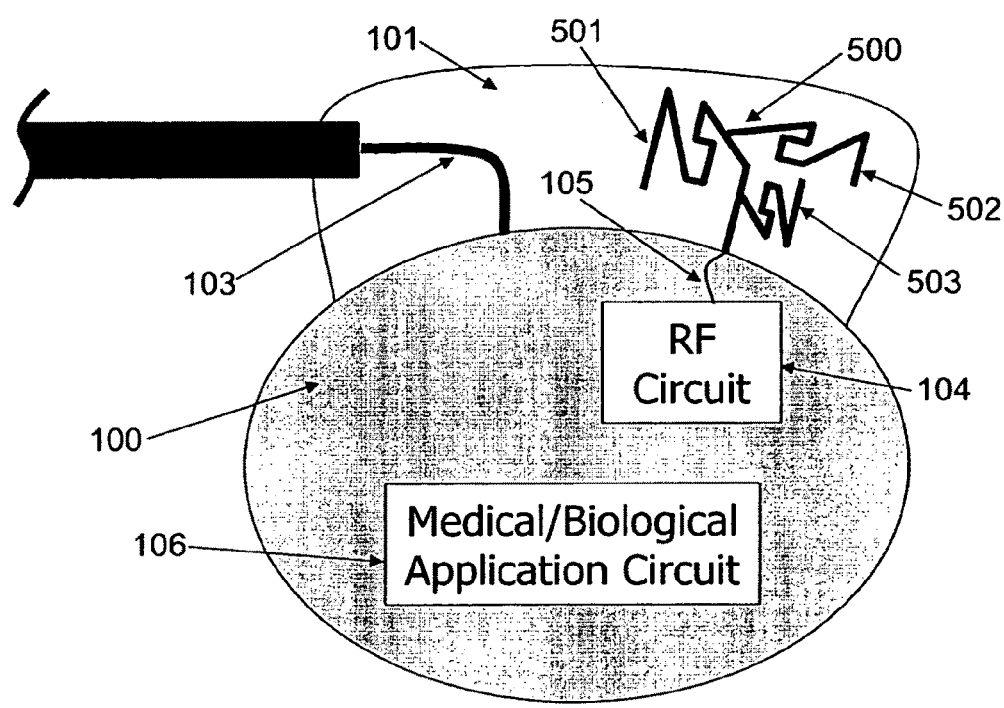
FIG. 5—Embodiment of an implantable medical device including a multibranch antenna according to the present invention.

FIG. 5 shows a multibranch antenna structure in an implantable device, where several curves, with not necessarily the same lengths, intersect each other at some points, and wherein at least one of said several curves comprises at least one portion that takes the form of a curve according to the present invention. In particular, the antenna (500) includes three arms (501-503), each of them being in the form of a curve according to the present invention. In this particular example the antenna takes the form of a monopole as in FIG. 1, with a single feeding port connected to an RF circuit (104) by means of a connection (105). The RF circuit (104) can also have one or more connections with an RF ground plane. By adjusting the number and lengths of the antenna arms (501-503) the frequency response of the antenna (500) can be tailored. In general, for a wide-band behavior, the length from the tips of the arms to the feeding point of the antenna will be similar. For a multiband response with no overlapping between frequency bands, the length of at least one, two, three, or more arms, or even each arm of the antenna, is associated mainly with the center frequency of a particular band within the antenna response. Such a multibranch arrangement is also compatible with other antenna topologies, such as for instance, but not limited to, a dipole, an inverted-F antenna, or a slot antenna.

Figure 6:
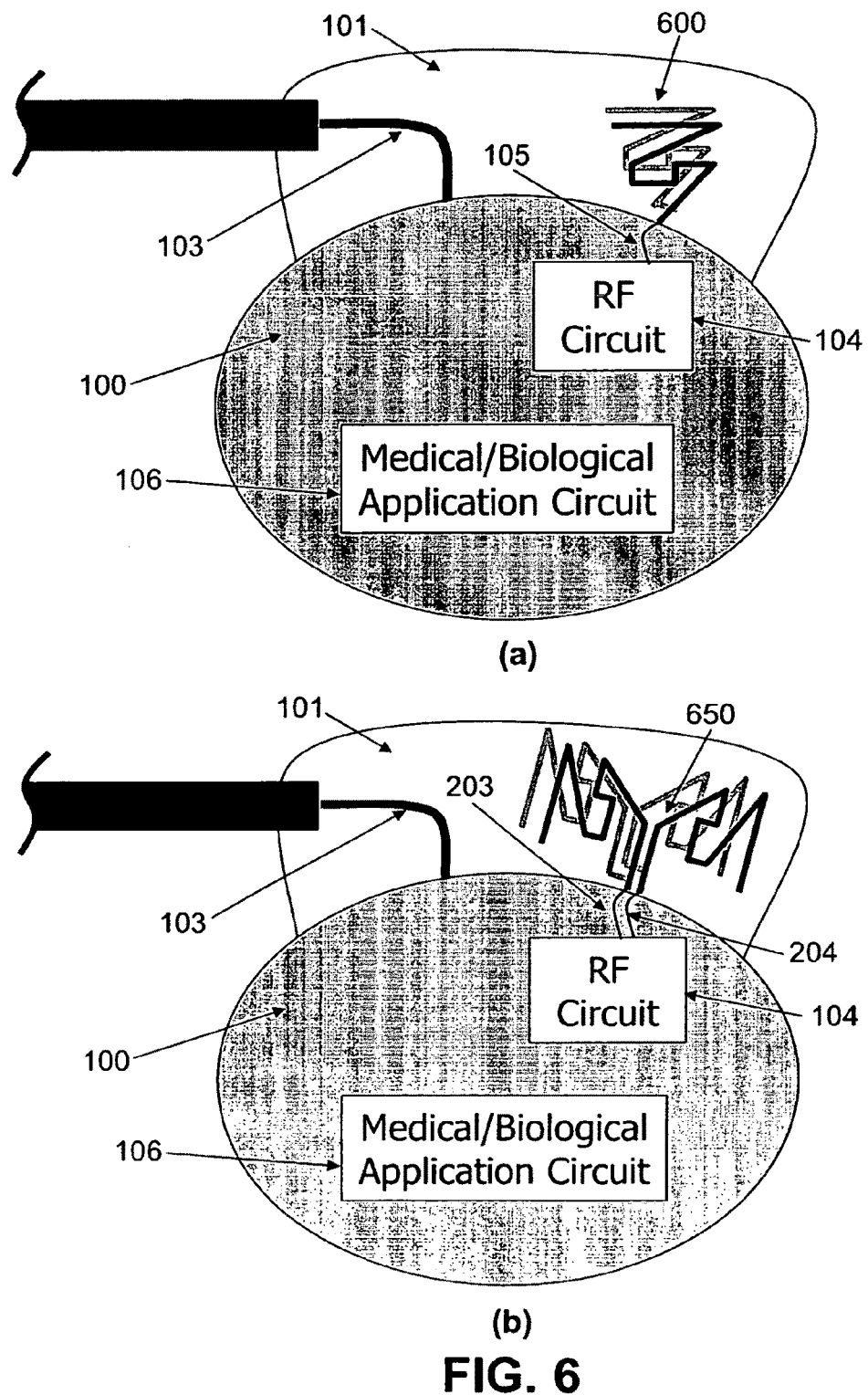
FIG. 6—Embodiments of an implantable medical device including an antenna according to the present invention, wherein the said antenna is (a) a dual-branch monopole antenna, and (b) a dual-branch dipole antenna.

Some other embodiments of a multibranch antenna integrated in an implantable medical device are presented in FIG. 6. The double-branch monopole antenna (600) and double-branch dipole antenna (650) in the embodiments presented in FIG. 6a and FIG. 6b respectively, use two branches of a similar length and shape that are arranged substantially parallel with respect to each other within the header (101) of the device. An advantage of such antenna design is the reduction of the ohmic losses of the antenna, and consequent improvement of the radiation efficiency. In some embodiments, the spacing between said substantially parallel arms will be the maximum available within the thickness of the device, to enhance the bandwidth and radiation efficiency of the antenna. In some embodiments, the shape and length of the branches will differ from one branch to the other, particularly in those embodiments in which a wide-band or a multi-band response of the device is required.

Figure 7:
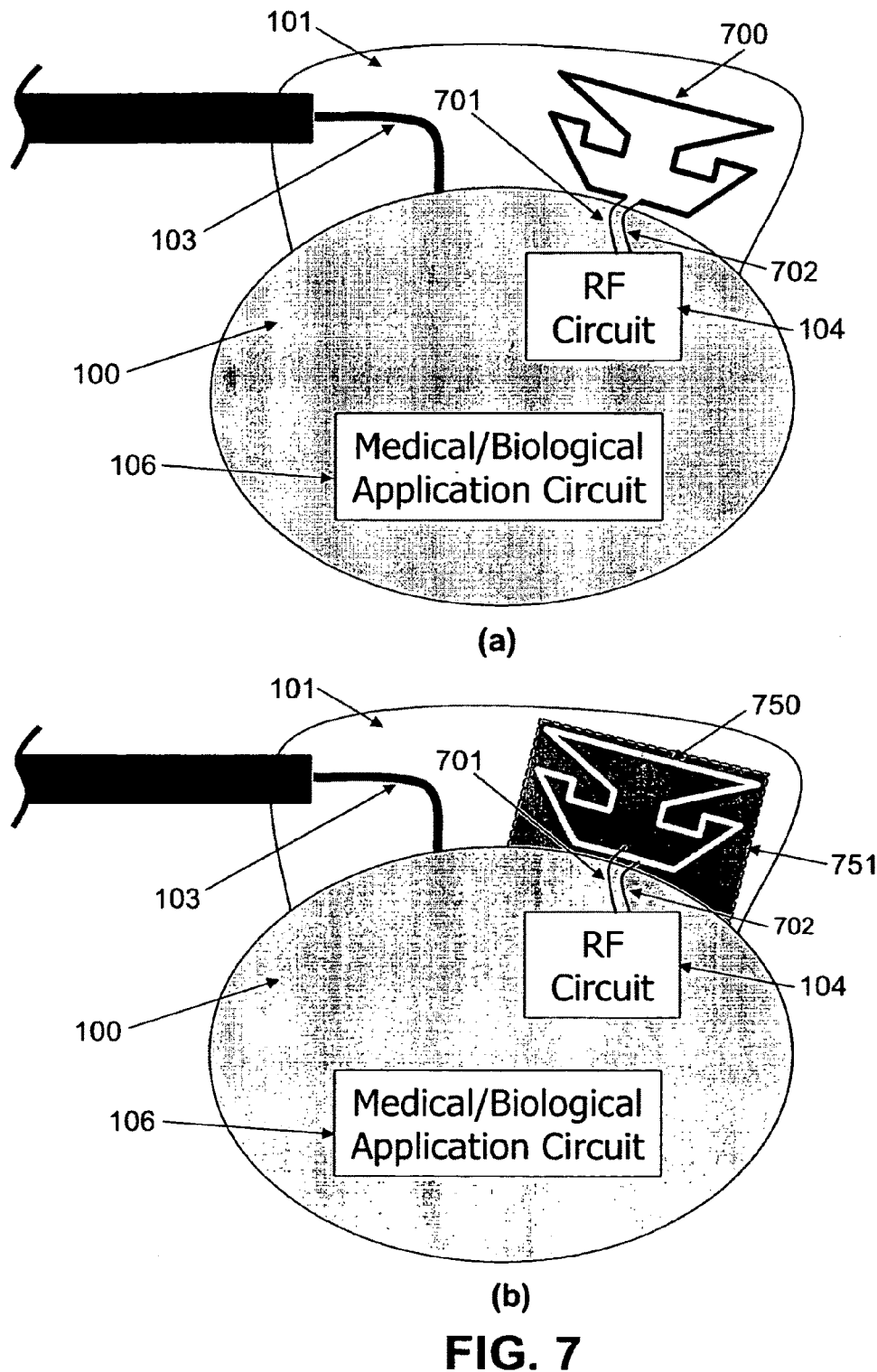
FIG. 7—Embodiments of an implantable medical device according to the present invention including: (a) a loop antenna; and (b) a slot or gap loop antenna.

FIG. 7a discloses an implantable medical device including a loop antenna (700) according to the present invention. In this case, the curve comprises 15 segments that are shorter than a tenth of the free-space operating wavelength and defines the perimeter of a loop, with two points of the loop providing the differential input terminal that is connected to an RF circuit (104) by means of conductors (701) and (702). For an improved performance of the system, the loop antenna (700) can be arranged within the header (101) of the device in such a way that it is substantially perpendicular to the contact surface between the metallic housing (100) and the header (101). In some embodiments, the loop will surround the whole implantable device to maximize the area enclosed inside the loop. In this later case, a non-conductive separation between the loop wire and the metallic parts of the implantable device will be kept, except optionally for one or more short-circuits to an RF ground.

FIG. 7b presents an embodiment including a gap or slot loop antenna. Similarly to the embodiments in FIG. 3 and FIG. 4, the antenna comprises a gap or slit (750) forming a closed loop that is created on a conducting pattern (751) within the header (101). The conducting pattern (751) is arranged substantially perpendicular to the contact surface between the metallic housing (100) and the header (101). For this embodiment, a feeding conductor will be connected inside the loop, while another one will be connected outside the loop. Preferably, both feeding conductors will be placed close to each other, at opposite edges of the slot.

Figure 8:
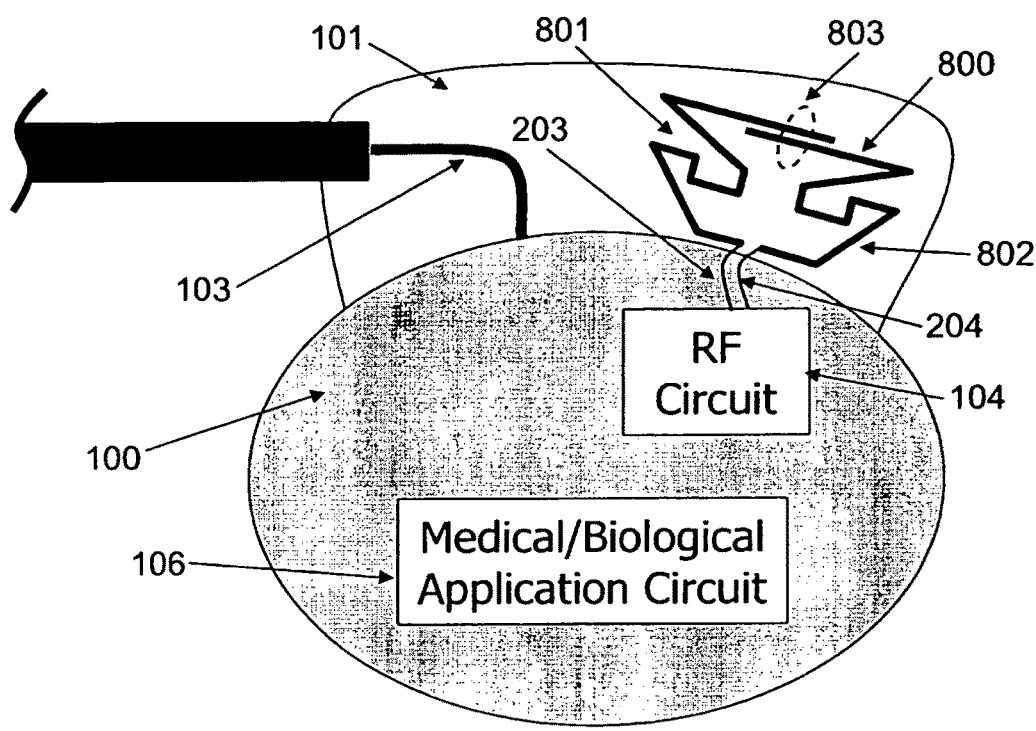
FIG. 8—Embodiment of an implantable medical device including a coupled dipole antenna according to the present invention.

The embodiment of an implantable device in FIG. 8 includes a coupled dipole antenna (800) with two arms (801) and (802) which are coupled together by means of a close proximity region (803). According to the present invention, the maximum distance between conductors in said close proximity region (803) should be less than one-tenth of the longest free-space operating wavelength of the antenna.

Figure 9:
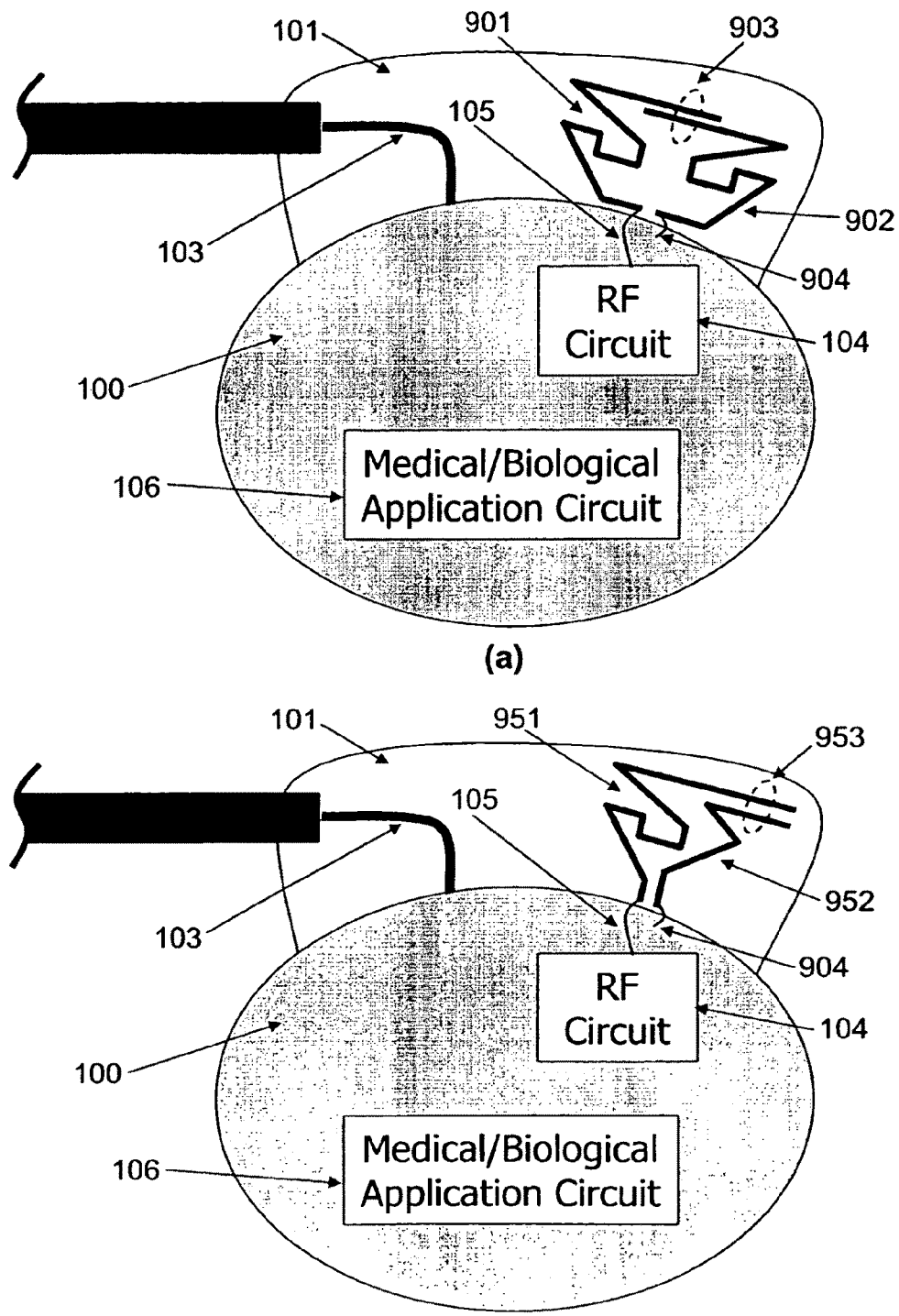
FIG. 9—Embodiments of an implantable medical device including an active monopole antenna and a parasitic monopole antenna according to the present invention, both monopoles coupled through a close proximity region.

FIG. 9 discloses two other embodiments where the implantable medical device includes an active monopole, such as (901) or (951), and at least one parasitic monopole, such as (902) or (952). In each embodiment, at least one of the active monopole and parasitic monopole is shaped as a curve according to the present invention. The parasitic monopoles (902) and (952) are grounded to an RF ground plane or counterpoise, which can comprise the housing (100) of the implantable device, or part of said housing. A first portion within the active monopole (901) or (951) is coupled to a second portion within the parasitic monopole (902) or (952), by means of a close proximity region (903) or (953), such that the maximum distance between said first portion and second portion in said region should be less than one-tenth of the longest free-space operating wavelength of the antenna. In some embodiments, such as that in FIG. 9b, the parasitic monopole will follow a path substantially close to the one of the active monopole, while in other embodiments, such as that in FIG. 9a, the parasitic path will be spaced away from the active one such as that the coupling is produced mainly only in said close proximity region (903). While in some embodiments the distance between the feeding point (105) in the active monopole and the ground connection (904) in the parasitic monopole will be substantially close (for instance closer than a tenth of the free-space operating wavelength), in other embodiments the spacing will be substantially larger and closer to the maximum available inside the plastic header to improve bandwidth and/or antenna efficiency.

While in some embodiments the conducting arms of the antennas will take the form of wires, in other embodiments a shaped metal strip will be preferred. A wider conductor will provide, in some embodiments, a wider bandwidth, an increased efficiency or a combination of both effects. Also, such wider metal strips better confine the near-fields present in the antenna such that the resonance effect is less affected by the surrounding environment; in this way, the implantable device can be installed in a wider range of different living bodies, or even in different regions comprising different types of body tissues with different electromagnetic properties.

Figure 10:
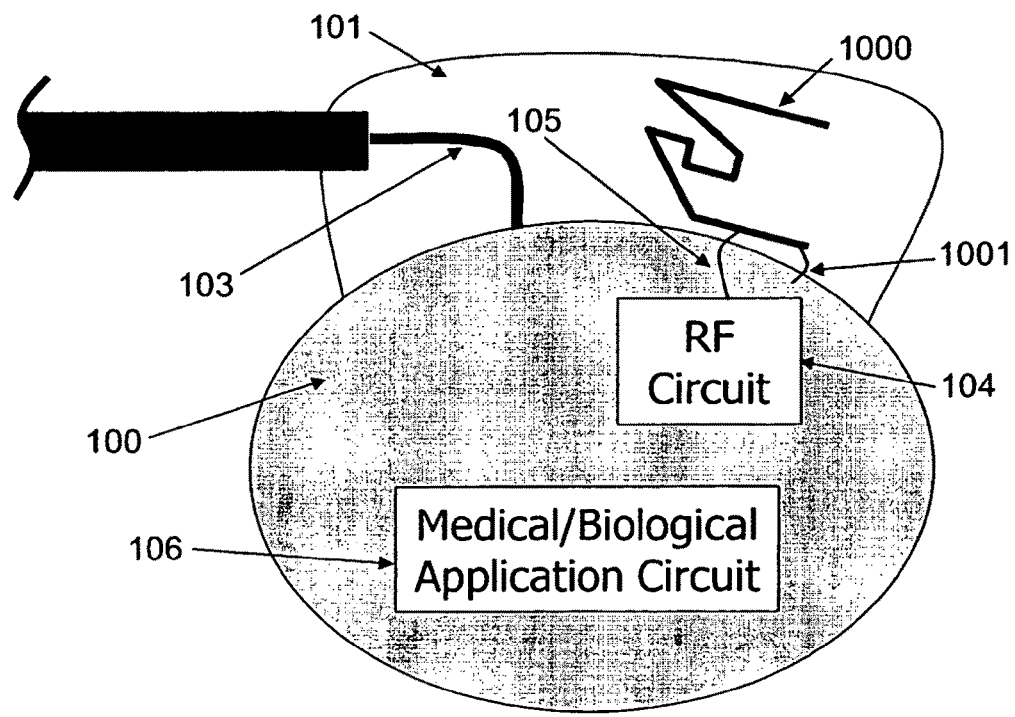
FIG. 10—Embodiment of an implantable medical device including an inverted-F antenna (IFA) according to the present invention.

FIG. 10 discloses an implantable medical device including an inverted-F antenna (IFA). Similarly to some previous embodiments discussed above, the antenna (1000) is arranged within the header (101) of the device, and the antenna (1000) is substantially perpendicular to the contact surface between the metallic housing (100) and the header (101). In this embodiment, the antenna (1000) is grounded at one of its tips, by means of at least one terminal (1001), to an RF ground plane that can comprise the housing (100) of the device. Also, the antenna (1000) is fed at an intermediate point of the antenna curve by means of a conducting terminal (105), such as for instance a feedthrough, that connects the antenna (1000) with an RF circuit (104) internal to the housing (100) of the implantable device. In such an embodiment, the relative position of the feeding terminal (105) and the grounding terminal (1001) can be advantageously used to tailor the antenna input impedance. The geometry of the wire of such an IFA antenna can be tailored according to the requirements of each implantable device and application. In those embodiments where it is required to reduce the profile of the protruding dielectric header, the main arm of the IFA (1000) will run substantially parallel to the housing (100) of the device. The spacing between said arm and said housing will be preferably small (about one or a few millimeters), although in those embodiments in which the efficiency and bandwidth are to be enhanced, such a spacing can be increased to a range from approximately 3 mm to approximately 10 mm or more. In those cases, the wire or strip forming said main arm of the IFA (1000) can also be bent to conformally adapt the contour of the housing of the device.

Also, in those embodiments in which the size of the antenna is to be reduced, such a wire or strip can be folded parallel to said housing so as to include at least five segments, or to include, for instance, a space-filling curve, a box-counting curve or a grid-dimension curve according to the present invention.

Figure 11:
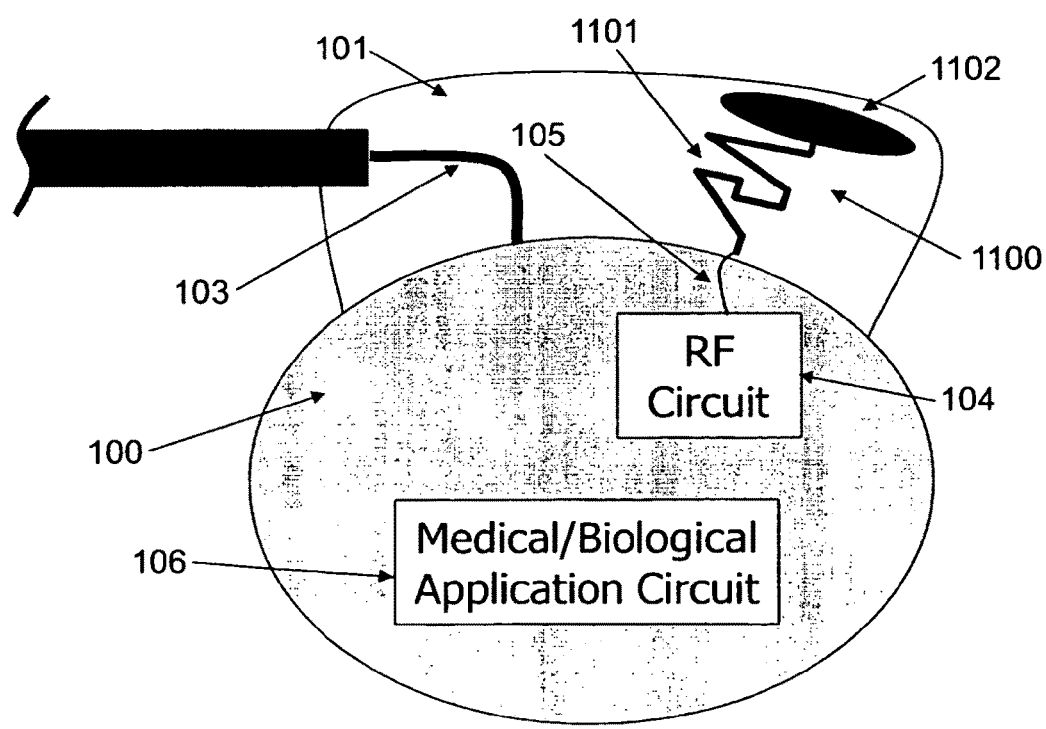
FIG. 11—Embodiment of an implantable medical device including a top-loaded monopole antenna according to the present invention.

Another embodiment shown in FIG. 11 discloses an implantable device including a top-loaded antenna. In this particular example, a monopole antenna has been considered, although other antenna configurations, such as for instance those described herein, are possible. In FIG. 11, the antenna (1100) comprises a conducting trace (1101) arranged substantially perpendicular to the contact surface between the metallic housing (100) and the header (101), and a conducting plate (1102) connected at one end of the conducting trace (1101) and arranged substantially perpendicular to said conducting trace (1101). According to the present invention, at least the conducting trace (1101) or a portion of the contour of the conducting plate (1102) is shaped as the above-mentioned curve with at least five segments, and/or as a space-filling curve (SFC), and/or as a box-counting curve, and/or as a grid dimension curve. An effect of the conducting plate (1102) is to cumulate electric charge at the end of the conducting trace (1101) connected to said conducting plate (1102), so that an electrical length of the antenna (1100) is increased (or, equivalently, a resonance frequency is lowered) with respect to the case in which there is no such conducting plate (1102) (as, for example, in FIG. 1).

Figure 12:
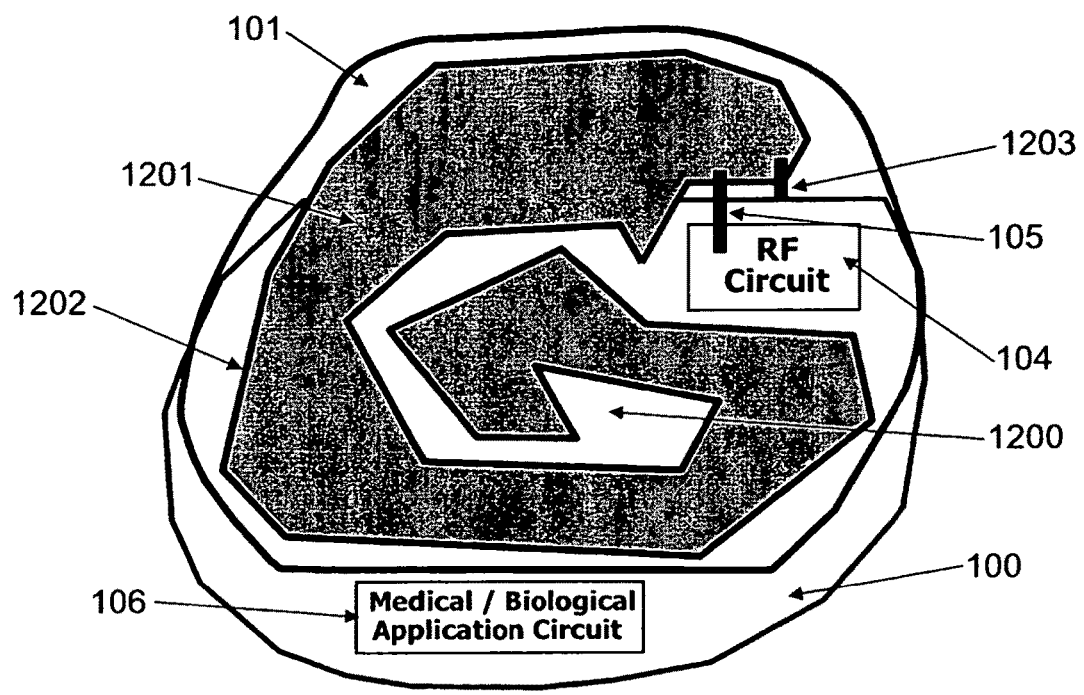
FIG. 12—Embodiment of an implantable medical device including an antenna comprising a conducting plate, wherein a curve according to the present invention defines at least a portion of the perimeter of the said conducting plate of the antenna.

FIG. 12 shows another embodiment of the present invention. In this case, the implantable device includes an antenna (1200) comprising a conducting plate (1201), wherein a curve (1202) as defined above defines at least a portion of the perimeter of said conducting plate (1201). A point within said conducting plate (1201) is chosen as the feeding point of the antenna (1200) and is connected, by means of a conducting terminal (105), to an RF circuit (104) internal to the housing (100) of the device.

Such a conducting pattern can be used in different ways: In those embodiments in which more than 50% of the area below the conducting plate (1201) is filled with a conducting material, such as for example the metallic housing (100) of the device, the antenna becomes a microstrip or patch antenna, the conducting material being the ground for the microstrip or patch antenna. In particular, the antenna also becomes a planar inverted-F antenna (PIFA) if, additionally, at least one conducting terminal (1203) to short the conducting plate (1201) to ground is included at any point within the conducting plate (1201). In the case of either a microstrip or patch arrangement, or in the PIFA case, the ground covering more than 50% of the area underneath the antenna (1200) is preferred. When there is no metallization on at least the 50% of the upper or lower projection of the conducting plate (1201), said conducting plate (1201) can constitute a monopole antenna. In this case, an RF circuit (104) of the implantable device can be connected to a conducting RF ground plane, which can optionally comprise the housing (100).

In a preferred embodiment including a microstrip or patch arrangement (including a PIFA arrangement), the characteristic pattern of the invention should preferably include a curve with at least fourteen or fifteen segments, with at least six or seven of them being shorter than one-twentieth of the free-space operating wavelength of the antenna, according to the present invention. This is necessary to achieve the desired degree of miniaturization that allows the integration of the antenna in a small area. The rest of the general conditions of the geometric aspects of the invention, as described above, apply to the microstrip patch and their shorted versions as well.

The geometry of the antenna in the present invention is not limited to being completely shaped by the characteristic curve of at least five segments. The curve needs only to define a portion or an aspect of the geometry, such as for instance a portion of the conducting strip or wire in case of a wire antenna such as a monopole or a dipole or an IFA, a portion of the slit in case of a slot or aperture antenna, or a portion of the antenna perimeter in case of a patch antenna.

Figure 14:
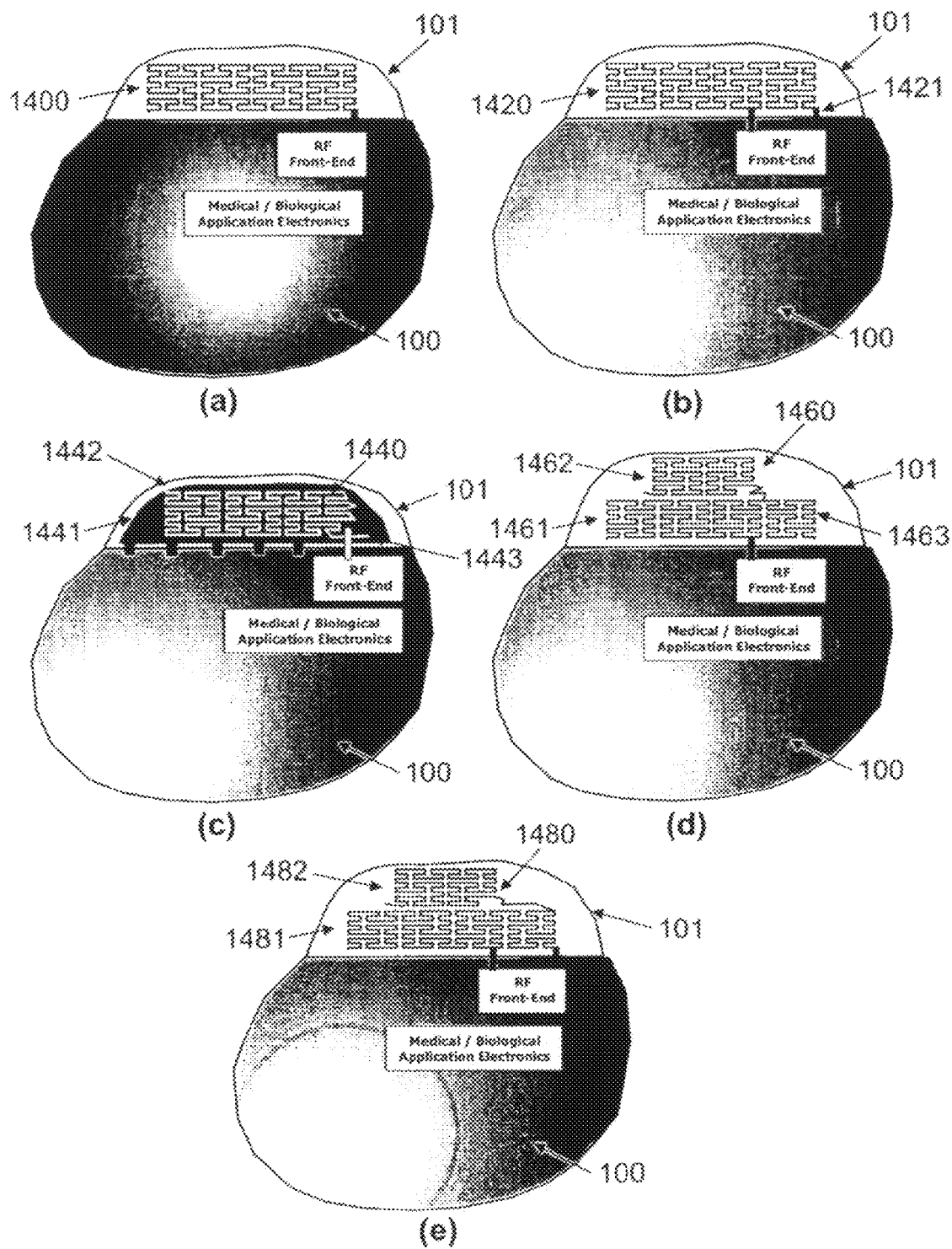
FIG. 14—Embodiments of an implantable medical device including a monopole antenna, or an inverted-F antenna (IFA) or a slot antenna with at least a portion shaped as a SZ curve according to the present invention.

FIGS. 14a through 14e show, without any limiting purpose, five examples of preferred embodiments of the invention. In all the cases at least a portion of the antenna pattern is defined by a space-filling curve. In some embodiments, such a curve will include an SZ (1400) or Hilbert curve. FIG. 14a depicts the case in which the integrated antenna is a monopole antenna (1400) arranged within the header (101) in a similar way to the one shown in FIG. 13b. The monopole antenna (1400) uses a substantial part of the maximum available space in the header (101), for maximum miniaturization of the antenna. FIG. 14b presents the shorted version (IFA) of the monopole antenna (1400) used in FIG. 14a. The terminal (1421) connects the antenna (1420) to the RF ground plane, and provides a means to control the input impedance of the antenna (1420). FIG. 14c shows a preferred embodiment including a slot antenna comprising a slit (1440) shaped as a space-filling curve practiced in a conducting pattern (1441). One or more conducting terminals connect the conducting pattern (1441) to the RF ground plane. Preferably, the slot will feature an open-end (1442) intersecting the contour of the conducting element (1441) enclosing said slot, and a shorted-end (1443) at the opposite end of the curve. The feeding schemes will preferably be analogous to those described for the embodiments in FIG. 3 and FIG. 4. FIG. 14d presents an embodiment including a multibranch space-filling monopole. The monopole (1460) comprises three branches (1461-1463), each of them being shaped as a space-filling curve, which makes it possible for the antenna (1460) to operate at three different frequency bands. Finally, FIG. 14e shows a multi-branch IFA (1480) comprising two branches (1481) and (1482), each of them being shaped as a space-filling curve.

Figure 15:
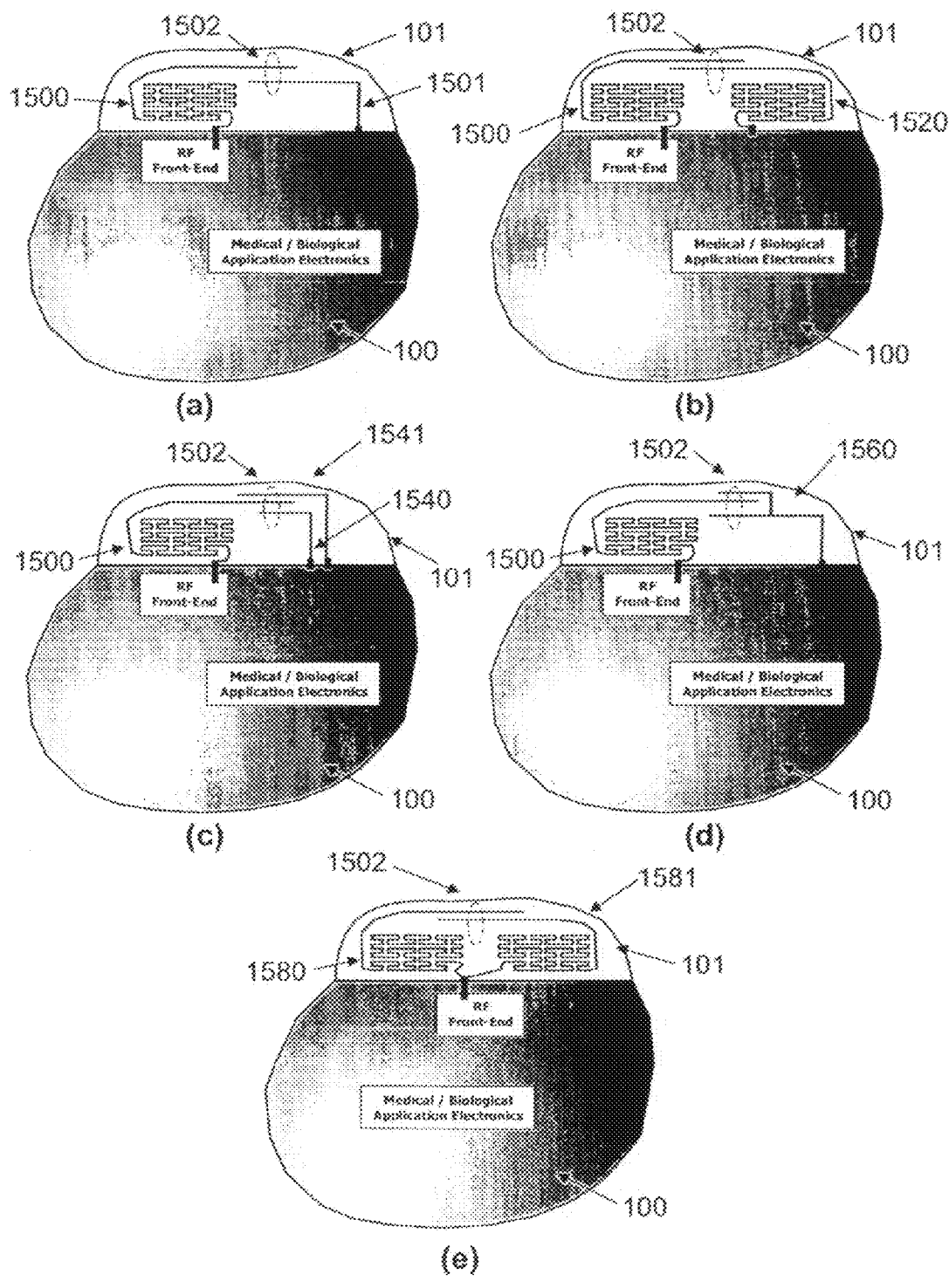
FIG. 15—Embodiments of an implantable medical device including coupled monopole antennas with at least a portion shaped as a SZ curve according to the present invention.

FIGS. 15a through 15e show five examples of preferred embodiments of an implantable medical device including coupled monopole antennas with at least a portion shaped as a space-filling curve. A curve based on the SZ curve is shown (without any limiting purpose). FIG. 15a comprises an active monopole (1500) which includes a portion shaped as space-filling curve, and a parasitic element (1501). A first portion within the active monopole (1500) is coupled to a second portion within the parasitic monopole (1501) by means of a close proximity region (1502). In FIG. 15b, and to further miniaturize the antenna, the parasitic monopole (1520) also includes a portion shaped as space-filling curve. In the embodiment of FIG. 15c, an active monopole (1500) is coupled to two or more parasitic monopoles, like for example (1540) and (1541) in the figure. This embodiment is advantageous in enhancing the control over the antenna impedance and bandwidth. In some embodiments where a wider bandwidth is desired, the length of at least two of the parasitic elements will be similar, while on the other hand a more substantial difference in length will be preferred in some embodiments in which a multi-resonance or multi-frequency response is desired. FIG. 15d presents another embodiment in which a parasitic monopole (1560) comprises a plurality of branches and wherein the active element is coupled to one or more of said plurality of branches. FIG. 15e shows an example of an implantable device in which the antenna comprises a first active monopole (1580) coupled to a second active monopole (1581). In this example, both the first and the second active monopoles (1580) and (1581) each comprise a portion shaped as a space-filling curve.

In the case of the embodiments shown in FIGS. 15a through 15e, the maximum distance between a first monopole and a second monopole within the close proximity region (1502) is preferably less than approximately one-tenth of the longest free-space operating wavelength of the antenna.

Figure 16:
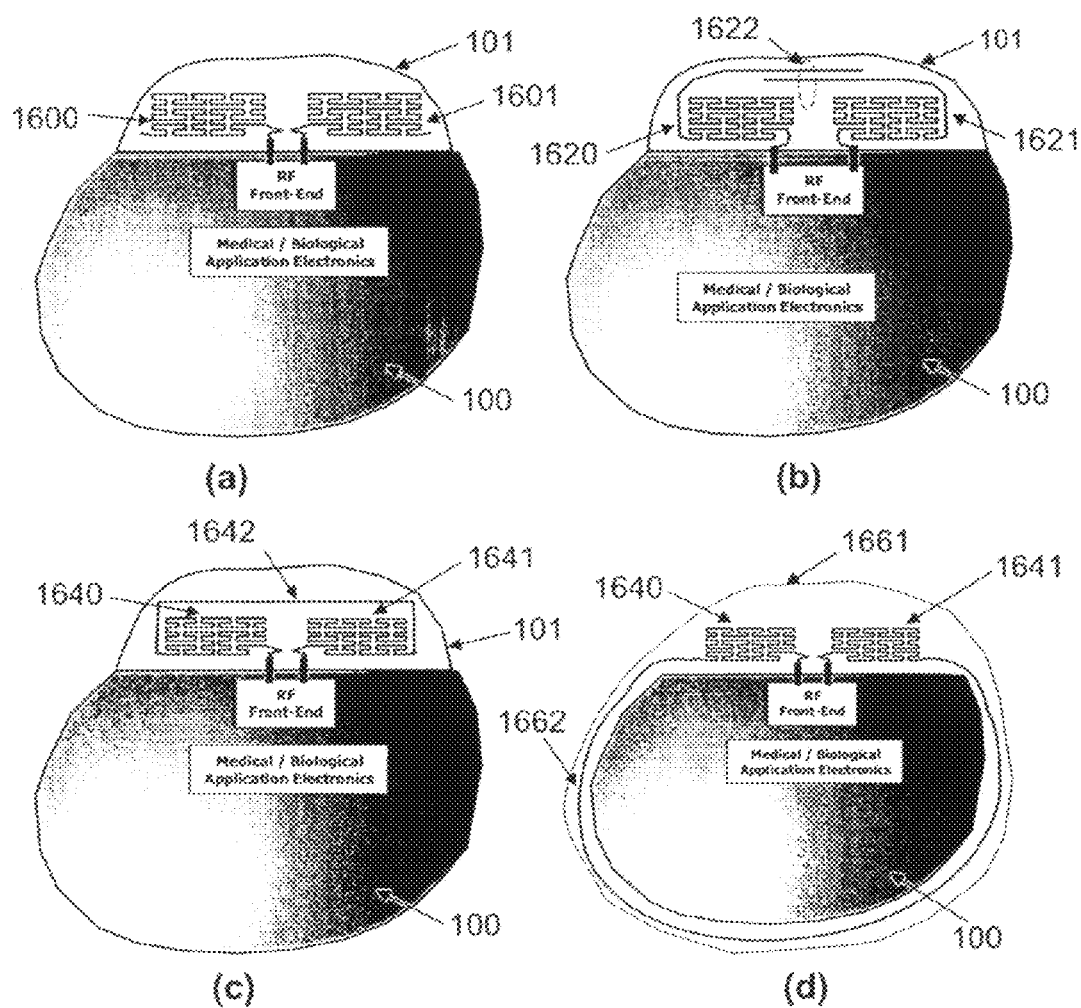
FIG. 16—Embodiments of an implantable medical device including dipole antennas with at least a portion shaped as a SZ curve according to the present invention.

FIGS. 16a through 16d represent some preferred embodiments of an implantable medical device including a dipole antenna. Each one of the arms of the dipole, (1600) and (1601), comprises a portion shaped as a curve according to the present invention. Additionally in FIG. 16b the two arms of the dipole, (1620) and (1621), are coupled to each other by means of a close proximity region (1622), which is advantageous in further miniaturizing the size of the antenna, or in enhancing the bandwidth and/or efficiency with respect to the dipole antenna in FIG. 16a. FIGS. 16c and 16d include a dipole antenna wherein the ends of each of the two arms, (1640) and (1641), are connected by means of a conducting trace or wire (1642) forming a folded dipole. In the case of FIG. 16d, the conducting trace or wire (1662) that connects the ends of the two arms of the dipole is wrapped around the housing (100) of the implantable medical device, advantageously using all the periphery of the device to enhance the electrical performance of the antenna. In this embodiment, the antenna is located within the dielectric compartment (1661).

Figure 17:
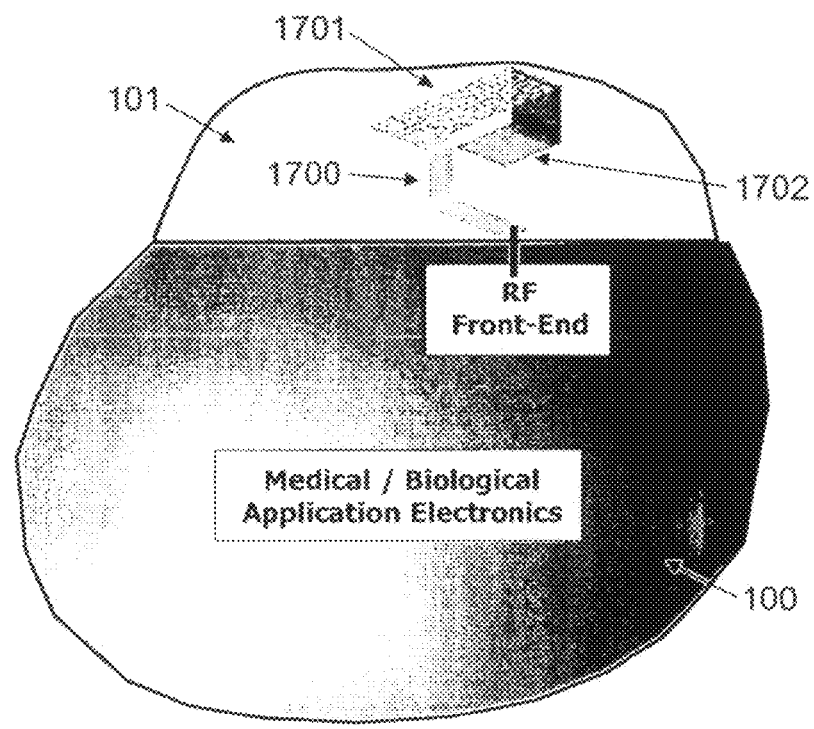
FIG. 17—Embodiment of an implantable medical device including a three-dimensional folded monopole according to the present invention.

FIG. 17 shows an embodiment of an implantable device including a three-dimensional or volumetric antenna (1700) comprising at least one portion (1701) that is shaped as a space-filling curve based on the Hilbert geometry. The antenna further comprises other portions formed by conducting strips and/or conducting plates. The folding nature of the antenna in more than two dimensions implies an efficient use the space available in the header of the implantable device. Moreover, it is advantageous to have a first portion (1701) of the antenna (1700) placed substantially parallel and in the projection (i.e., above or underneath) of a second portion (1702) of the antenna (1700), so that there is a close proximity region in which said first portion (1701) is coupled to said second portion (1702), and the electrical performance of the antenna is enhanced. The maximum distance between said first portion (1701) and said second portion (1702) within the close proximity region is preferably less than approximately one-tenth of the longest free-space operating wavelength of the antenna.

A further aspect of the invention has to do with the compatibility of the antenna design with materials used typically for implantable devices.

Metals commonly used in implants, either as pure elements or as alloys, comprise platinum, iridium, niobium, gold, iron (in stainless steel alloys), vanadium, cobalt, aluminum and zirconium. In some embodiments, a metal alloy made of approximately of 90% platinum and approximately 10% iridium can advantageously be used to fabricate the conducting trace, conducting wire, conducting strip, and/or conducting plate of the antenna. In some other embodiments, niobium may be preferred to fabricate the antenna, as it has a slightly higher conductivity than the above-mentioned alloy of platinum and iridium.

Generally, it is desirable to minimize the ohmic losses of the antenna by selecting metals or alloys with high conductivity. In some embodiments, a metal or alloy with a conductivity of approximately $10^7$ S/m or higher will be advantageous to fabricate the conducting trace, conducting wire, and/or conducting plate of the antenna according to the present invention.

Plastic materials and dielectrics typically used for implantable medical devices comprise, for instance, and without limitation, thermoplastic urethane (tecothane), polytetrafluoroethylene (PFTE), expanded polytetrafluoroethylene (EFTE) and polyetheretherketone (PEEK). In some embodiments, it will be preferable to use dielectric materials with a dissipation factor (loss tangent) smaller than approximately $10^{-2}$ in at least one of the frequency bands of the antenna, at least in a portion of the implantable device in the proximity of the antenna.

The above description relates to the main aspects of the invention that contribute to the antenna miniaturization and its efficient integration on an implantable medical device. It should be noted that not every folded structure would provide the desired degree of antenna miniaturization; packing a large length of wire or conducting material in any arrangement will not always provide an efficient behavior of the antenna, due to coupling between segments and bends, and due to an inefficient use of the available space. The present invention provides the necessary degree of compactness to achieve the desired degree of integration of the antenna into an implantable medical device.

In some cases, the antenna integrated in the wireless implantable medical device will operate in at least one frequency band comprised in the range from approximately 300 MHz up to approximately 6 GHz, with any subinterval within that range included. Preferably, one or more of the ISM (industrial, scientific, medical) frequency bands of the radioelectric spectrum will be used. In some preferred embodiments, the wireless implantable medical device will be capable of operating at one, two, three or more of the frequency bands typically used for telemetry services, such as for instance and without limitation:

Medical Implant Communication Systems (MICS) bands, like for example the 402-405 MHz band.
Wireless Medical Telemetry Services (WMTS) bands, like for example the 608-614 MHz band, the 139-1400 MHz band, or the 1427-1432 MHz band.
Industrial, Scientific, Medical (ISM) unlicensed bands, like for example the 915 MHz ISM band (902-928 MHz), 2.4 GHz ISM band (2400-2500 MHz), or 5.7 GHz ISM band (5650-5925 MHz).
Unlicensed general telemetry bands, like for example the 433.05-434.79 MHz band, or the 868-870 MHz band
VHF and UHF bands, like for example the UHF PLMRS bands from 450 to 470 MHz.

Figure 18:
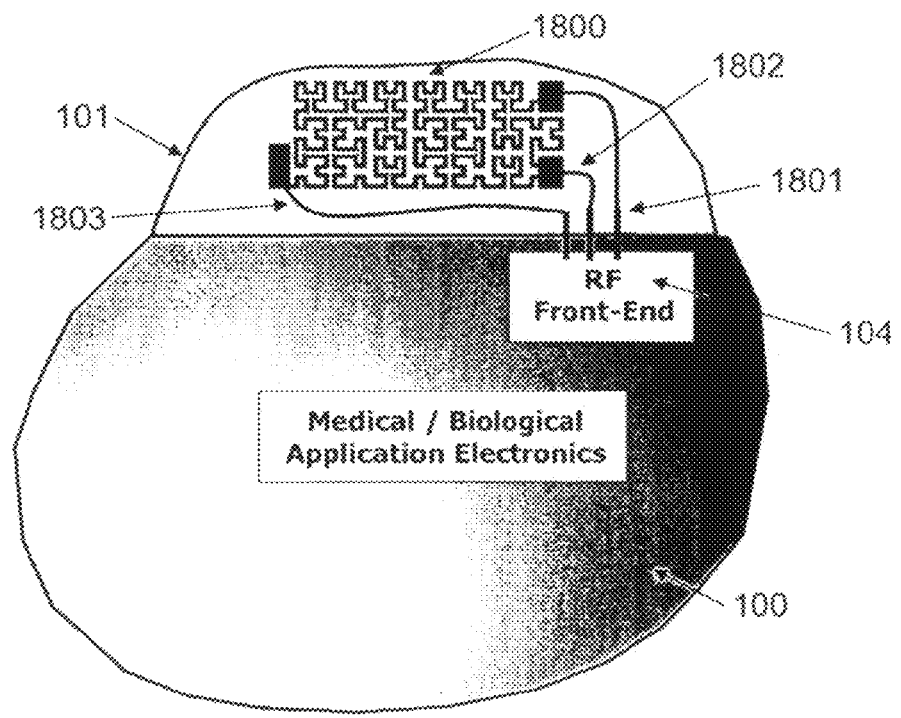
FIG. 18—Embodiment of an implantable medical device including a monopole antenna according to the present invention comprising a plurality of feeding terminals.

In some embodiments of the implantable device including an antenna, such as for example the one depicted in FIG. 18, the antenna (1800) comprises a plurality of terminals (1801-1803), that are available to an RF circuit (104) included in the implantable device for feeding the antenna. This feature can be advantageous if said RF circuit (104) can select the terminal used for feeding the antenna among the plurality of available terminals (for example, by means of a switching component or circuit) depending on the frequency band, or communication service, that is used in the wireless link between the implanted device and an external unit. An implantable medical device including such an antenna arrangement would allow the same implantable device to be commercialized in geographical domains with different allocation of radio services (e.g., the antenna may cover the 860 MHz unlicensed band in Europe or the 915 MHz ISM band in the U.S.)

Another aspect of the invention relates to radiofrequency communication systems comprising an implantable medical device with an integrated antenna.

Remote monitoring of the medical condition of a patient, like for example from the patient's home, can be implemented using a wireless implantable medical device such as the one disclosed above. The implanted device can communicate via a radiofrequency link with an external unit that records information about the patient (such as for instance vital signals, therapy parameters, or medication dosage) over time. The external unit can relay some of this information by means of a communication network (such as for instance, but not limited to, the cellular phone network) to a health-monitoring center (such as a physician's office, a hospital or a health center), where for example a physician can monitor the evolution of the patient and determine if changes in the therapy are necessary. In that case, the new therapy instructions can be transmitted from the health-monitoring center to the patient's external unit, which in turn can re-program the implantable medical device to carry out the new therapy.

Such a remote monitoring method provides a basis for real-time information of the medical condition of the patient, which can be advantageously used to contact an emergency service in the event that the medical condition of a patient aggravates. In some cases, it can also be applied to monitor the level of charge of the battery of the implantable device. Knowing precisely when this level drops below a safety threshold is useful to determine when the patient has to undergo surgery to have the battery of the implantable medical device replaced, while avoiding the risk of battery exhaustion. This has benefits both on the well-being of the patient and on the economic savings related to surgery.

Wireless identification of an individual (for instance a human being, or an animal) can also be implemented using an implantable device with an antenna according to the present invention. Such a system can comprise a wireless implantable device that includes an electronic circuit that stores information about the individual (such as for example personal data, or the medical history of the individual). The implanted device can be programmed from an external unit by means of a wireless link to either write information into the device, or read information from the device, or modify the information stored in the device. Additionally, other external units with read-only capabilities can interrogate the implanted device.

In some embodiments of such a system, the implantable device with an integrated antenna comprised in the wireless identification system is a medical device that performs some therapeutic functionality. An external unit of the wireless identification system can advantageously be used to detect the presence of an individual carrying the said implantable medical device in the proximity of an area in which strong electromagnetic fields (such as for instance the fields created by a metal detector arch, or a magnetic resonance imaging system) could interfere with the proper functioning of the implanted medical device. Upon detection, the system can take protective measures (such as for instance triggering an acoustic or visual warning signal, or shutting down the electromagnetic field source) to prevent the malfunctioning of the implanted medical device.

The features of the miniature wireless implantable devices described in the present invention are open a wide range of possibilities in terms of methods for medical assistance, local or remote treatment and monitoring. Such methods can be linked to new commercial services enabled by the features of the disclosed implantable medical device. On one hand, the commercialization of the miniature implantable device per se will provide a business competitive advantage due to the fact that both patients and physicians prefer smaller and safer devices with enhanced monitoring and control features. On the other hand, the remote access to real-time physical, physiological and/or biological information of the patient will make it possible to develop business methods providing medical surveillance, on-line and/or fast assistance services. Furthermore, significant economic savings can be obtained for insurance companies and/or public or private healthcare organizations by developing prevention programs that might detect, in advance, potential diseases, adverse reactions to drugs or the worsening of some already existing illness, through the use of such wireless implantable devices. Also, the remotely controlled implantable device can be used to deliver drugs, more efficiently, in the required doses and at the required moments, which might imply economic savings in the delivery of particularly costly drugs, and at the same time provide for a better control on the dosage of those drugs, which might present some degree of toxicity or potentially risky adverse effects.

The invention claimed is:

1. A wireless implantable medical device comprising:
a device housing;
at least one radio frequency circuit for radio frequency communication of a monitoring signal with an external unit;
at least one antenna;
at least one terminal to electromagnetically couple said at least one antenna to said at least one radio frequency circuit; and
a dielectric compartment that encompasses at least a portion of said at least one antenna and at least a portion of at least one therapy-lead;
said at least one antenna comprises a conducting pattern, at least a portion of which is shaped as a curve, wherein said curve comprises at least five segments, wherein each of said at least five segments forms an angle with each adjacent segment in said curve, wherein at least three of the at least five segments of said curve are shorter than one-fifth of the longest free-space operating wavelength of the antenna, wherein each angle between adjacent segments is less than 180°, and at least two of the angles between adjacent sections are less than approximately 115°;
said curve is arranged such that at least two of the angles are defined respectively in the clockwise and counter-clockwise directions at opposite sides of said curve to minimize an inductive coiling effect;
wherein said at least two angles are smaller than 180°; and
the at least one therapy-lead comes out from the device housing via feedthroughs into a region covered by the dielectric compartment.

2. A device according to claim 1, wherein at least three of the at least five segments of said curve are shorter than one-tenth of the longest free-space operating wavelength of the antenna.

3. A device according to claim 2, wherein a majority of the at least five segments of said curve are shorter than one-fifth of the longest free-space operating wavelength of the antenna.

4. A device according to claim 1, wherein said curve is fitted over a flat surface.

5. A device according to claim 1, wherein said curve is fitted over a curved surface.

6. A device according to claim 1, wherein said curve is a curve selected from the group consisting essentially of the Hilbert, Peano, SZ, ZZ, HilbertZZ, Peanoinc, Peanodec, and PeanoZZ curves.

7. A device according to claim 1, wherein the segments of the curve are arranged in a dissimilar way with respect to the entire curve, whereby the curve is not a self-similar curve.

8. A device according to claim 1, wherein the curve has a box-counting dimension larger than 1.15.

9. A device according to claim 8, wherein the curve has a box-counting dimension larger than 1.5.

10. A device according to claim 9, wherein the curve has a box-counting dimension larger than 1.6.

11. A device according to claim 1, wherein the curve has a grid dimension larger than 1.15.

12. A device according to claim 11, wherein the curve has a grid dimension larger than 1.5.

13. A device according to claim 12, wherein the curve has a grid dimension larger than 1.65.

14. A device according to claim 1, wherein the antenna fits in a rectangle the largest side of which has a length that does not exceed one-fifth of the longest free-space operating wavelength of the antenna.

15. A device according to claim 14, wherein the antenna fits in a rectangle the largest side of which has a length that does not exceed one-twentieth of the longest free-space operating wavelength of the antenna.

16. A device according to claim 1, wherein the antenna is a monopole antenna wherein said conducting pattern comprises at least one conducting arm of said monopole antenna, and wherein at least a portion of said arm is shaped as said curve.

17. A device according to claim 1, wherein the antenna comprises at least one active monopole and at least one parasitic monopole, wherein at least one of said monopoles comprises a portion shaped as said curve, wherein said at least one active monopole is coupled to said at least one parasitic monopole by means of a close proximity region in which the distance between said at least one active monopole and said at least one parasitic monopole is less than a tenth of the longest free-space operating wavelength of the antenna, said at least one parasitic monopole being coupled to a ground plane of the device.

18. A device according to claim 1, wherein the antenna is a dipole antenna comprising at least two conducting arms.

19. A device according to claim 18, wherein at least two of said conducting arms are connected by a conducting element selected from the group comprising a conducting trace and a conducting wire.

20. A device according to claim 18, wherein said dipole antenna is a coupled dipole antenna comprising two arms coupled together by means of a close proximity region where the distance between the two arms in said region is less than a tenth of the longest free-space operating wavelength of the antenna.

21. A device according to claim 1, wherein the antenna is a three-dimensional antenna.

22. A device according to claim 1, wherein the antenna is a top-loaded antenna comprising at least one conducting trace and one conducting plate at the end of said conducting trace, at least one of said conducting trace and conducting plate including a portion shaped as said curve.

23. A device according to claim 1, wherein the antenna comprises a first portion that protrudes from the device housing, and a second portion substantially perpendicular to said first portion, said second portion being a substantially two-dimensional portion, said second portion being substantially located in a plane perpendicular to a contact area between said device housing and the dielectric compartment.

24. A device according to claim 1, wherein the antenna is a slot antenna.

25. A device according to claim 24, wherein the slot antenna comprises at least one slot in the device housing, said device housing being a metallic housing.

26. A device according to claim 25, wherein said at least one slot is covered by a dielectric material.

27. A device according to claim 1, wherein the antenna is a loop antenna.

28. A device according to claim 1, wherein the antenna is an inverted-F antenna.

29. A device according to claim 1, wherein the antenna is a patch antenna.

30. A device according to claim 1, wherein said antenna comprises at least one conducting plate, the perimeter of said plate comprising at least one portion shaped as said curve.

31. A device according to claim 30, wherein said conducting plate comprises at least one portion shaped as said curve, said portion comprising at least 14 segments, at least 6 of said segments having a length shorter than one twentieth of the longest free-space operating wavelength of the antenna.

32. A device according to claim 1, wherein the antenna is a microstrip antenna.

33. A device according to claim 1, further comprising a conducting ground plane, the radio frequency circuit being connected to the ground plane.

34. A device according to claim 1, wherein the device housing is a metallic housing.

35. A device according to claim 33, wherein at least a part of said ground plane is housed inside said metallic housing and insulated from said metallic housing.

36. A device according to claim 33, wherein said ground plane comprises at least a part of said metallic housing.

37. A device according to claim 1, wherein the antenna is embodied in a metal layer housed in said dielectric compartment.

38. A device according to claim 1, wherein the antenna is embodied as a metal trace on a surface inside said dielectric compartment.

39. An antenna according to claim 1, wherein the conducting pattern comprises at least one metal strip.

40. A device according to claim 1, wherein the antenna comprises a plurality of terminals arranged so that the radio frequency circuit can be selectively connected to one of said terminals, in accordance with a frequency band to be used for communication between the device and an external unit.

41. A device according to claim 1, wherein said at least one antenna is made up of a metal with a conductivity of at least $10^7$ S/m.

42. A device according to claim 41, wherein said metal is selected from the group consisting of platinum, iridium, niobium, gold, iron, vanadium, cobalt, aluminum, zirconium and niobium.

43. A device according to claim 1, wherein said dielectric compartment is at least partially made of a material selected from the group consisting of thermoplastic urethane, polytetrafluoroethylene, expanded polytetrafluoroethylene and polyetheretherketone.

44. A device according to claim 1, wherein said dielectric compartment includes at least one cavity for insulating the antenna from body tissues, said cavity at least partially encompassing the antenna.

45. A device according to claim 44, wherein said cavity is substantially empty.

46. A device according to claim 44, wherein said cavity is at least partially filled with a biocompatible material having a dielectric constant not higher than a maximum value selected from the group consisting of 4.0, 3.8, 3.6, 3.4, 3.2, 3.0, 2.8, 2.6, 2.4, 2.2, 2.0, 1.8, 1.6, 1.4 and 1.2.

47. A device according to claim 1, wherein the device is at least partially coated with a biocompatible dielectric material having a dissipation factor smaller than $10^{-2}$, or $5\times10^{-3}$, or $10^{-3}$, or $5\times10^{-4}$, or $10^{-4}$ for at least one operating frequency of the antenna.

48. A device according to claim 47, wherein the device is at least partially coated with a biocompatible dielectric material having a dielectric constant not higher than a maximum value selected from the group consisting of 4.0, 3.8, 3.6, 3.4, 3.2, 3.0, 2.8, 2.6, 2.4, 2.2, 2.0, 1.8, 1.6, 1.4 and 1.2.

49. A device according to claim 1, further comprising electronic circuitry that provides a medical function, said electronic circuitry being functionally associated with the radio frequency circuit so as to receive signals and/or data from said radio frequency circuit and/or so as to forward signals and/or data to said radio frequency circuit.

50. A device according to claim 49, wherein said device is capable of operating at one, two, three or more frequency bands used for telemetry services.

51. A device according to claim 49, wherein said electronic circuitry is arranged for monitoring one or more physiological variables by means of at least one sensor.

52. A device according to claim 49, wherein said electronic circuitry is arranged for applying stimuli to body by means of at least one actuator.

53. A device according to claim 49, wherein said electronic circuitry is arranged to overcome an impairment of a physiological functionality.

54. A device according to claim 49, wherein said electronic circuitry is a programmable electronic circuit, arranged to be programmed from an external programming unit through said radio frequency circuit.

55. A device according to claim 1, wherein the curve comprises segments that are arranged in an irregular way.

56. A device according to claim 1, wherein the curve comprises segments that are arranged in a substantially non-periodic way.

57. A device according to claim 1, wherein the curve comprises segments that are arranged in a dissimilar way.

58. A device according to claim 1, wherein said at least one antenna is made up of a metal alloy with a conductivity of at least $10^7$ S/m.

59. A device according to claim 58, wherein said metal alloy comprises at least one metal selected from the group consisting of platinum, iridium, niobium, gold, iron, vanadium, cobalt, aluminum, zirconium and niobium.

60. A wireless implantable medical device comprising:
a metallic housing, an electronic circuit that provides a medical function, a radio frequency circuit for radio frequency communication, a power source, an antenna, a radio frequency ground plane, a first terminal to electromagnetically couple the antenna to the radio frequency circuit;
a second terminal to electromagnetically couple said radio frequency ground plane to the radio frequency circuit, and a dielectric header that encompasses at least a portion of said antenna;
wherein said antenna comprises a conducting pattern, at least a portion of which includes a curve, said curve being shaped as a space-filling curve and featuring a box-counting dimension larger than 1.15;
wherein said curve is arranged such that at least two of the angles are defined respectively in the clockwise and counter-clockwise directions at opposite sides of said curve;
wherein said at least two angles are smaller than 180°;
said antenna comprising a first portion and a second portion, wherein said first portion protrudes from said metallic housing, and wherein the second portion is substantially perpendicular to said first portion; with said second portion arranged substantially perpendicular to the contact surface between the metallic housing and said dielectric header to minimize the projection of the second portion on the metallic housing;
wherein said antenna is an unbalanced antenna selected from the group consisting essentially of: monopole, IFA, patch, PIFA, and slot; and with said ground plane being coupled either through direct contact or electromagnetic coupling to the metallic housing at RF frequencies; and
wherein said wireless implantable medical device is used as part of a system to provide remote monitoring of the medical condition of a human being, in which said wireless implantable medical device implements the functionality of cardiac rhythm management, and communicates with at least one external unit via a radiofrequency link operating at least at one of the ISM frequency bands.

61. A radiofrequency communication system comprising at least one remote unit, wherein the radiofrequency communication system further comprises at least one wireless implantable medical device, the wireless implantable medical device comprising:
a device housing;
at least one radio frequency circuit for radio frequency communication of a monitoring signal with an external unit;
at least one antenna;
at least one terminal to electromagnetically couple said at least one antenna to said at least one radio frequency circuit;
a dielectric compartment that encompasses at least a portion of said at least one antenna, wherein said at least one antenna comprises a conducting pattern, at least a portion of which is shaped as a curve, wherein said curve comprises at least five segments, wherein each of said at least five segments forms an angle with each adjacent segment in said curve, wherein at least three of the at least five segments of said curve are shorter than one-fifth of the longest free-space operating wavelength of the antenna, wherein each angle between adjacent segments is less than 180°, and at least two of the angles between adjacent sections are less than approximately 115°;
wherein said curve is arranged such that at least two of the angles are defined respectively in the clockwise and counter-clockwise directions at opposite sides of said curve to minimize an inductive coiling effect;
wherein said at least two angles are smaller than 180°;
said at least one antenna is arranged substantially perpendicular to a contact surface between the device housing and the dielectric compartment to reduce the capacitive coupling to the device housing; and
wherein said at least one remote unit is arranged for radio frequency communication with said at least one wireless implantable medical device.

62. A system according to claim 61, wherein said remote unit comprises means for remotely reprogramming said device.

63. A system according to claim 61, wherein said remote unit comprises means for receiving data from said device and for processing said data.

64. A system according to claim 61, said system being a medical remote monitoring system.

65. A system according to claim 61, said system being a wireless identification system.

66. Use of a wireless implantable medical device for monitoring at least one physiological variable of a human being or an animal, the wireless implantable medical device comprising:
- a device housing;
- at least one radio frequency circuit for radio frequency communication of a monitoring signal with an external unit;
- at least one antenna;
- at least one terminal to electromagnetically couple said at least one antenna to said at least one radio frequency circuit;
- a dielectric compartment that encompasses at least a portion of said at least one antenna, wherein said at least one antenna comprises a conducting pattern, at least a portion of which is shaped as a curve, wherein said curve comprises at least five segments, wherein each of said at least five segments forms an angle with each adjacent segment in said curve, wherein at least three of the at least five segments of said curve are shorter than one-fifth of the longest free-space operating wavelength of the antenna, wherein each angle between adjacent segments is less than 180°, and at least two of the angles between adjacent sections are less than approximately 115°;
- wherein said curve is arranged such that at least two of the angles are defined respectively in the clockwise and counter-clockwise directions at opposite sides of said curve to minimize an inductive coiling effect;
- said at least one antenna protrudes from the device housing;
- at least one end of the at least one antenna is placed substantially far from the device housing to improve a performance of the at least one antenna; and
- wherein said at least two angles are smaller than 180°.

67. Use of a wireless implantable medical device for applying stimuli to a body of a human being or an animal, the wireless implantable medical device comprising:
- a device housing;
- at least one radio frequency circuit for radio frequency communication of an actuation signal with an external unit;
- at least one antenna;
- a radio frequency (RF) ground plane;
- at least one terminal to electromagnetically couple said at least one antenna to said at least one radio frequency circuit; and
- a dielectric compartment that encompasses at least a portion of said at least one antenna, wherein said at least one antenna comprises a conducting pattern, at least a portion of which is shaped as a curve, wherein said curve comprises at least five segments, wherein each of said at least five segments forms an angle with each adjacent segment in said curve, wherein at least three of the at least five segments of said curve are shorter than one-fifth of the longest free-space operating wavelength of the antenna, wherein each angle between adjacent segments is less than 180°, and at least two of the angles between adjacent sections are less than approximately 115°;
- wherein said curve is arranged such that at least two of the angles are defined respectively in the clockwise and counter-clockwise directions at opposite sides of said curve;
- wherein said at least two angles are smaller than 180°;
- said at least one antenna is grounded via at least one grounding terminal to the RF ground plane to control an input impedance of said at least one antenna; and
- a region of the wireless implantable medical device is coated with a layer of biocompatible material to enhance insulation between the wireless implantable medical device and surrounding body tissues.

* * * * *

UNITED STATES PATENT AND TRADEMARK OFFICE
CERTIFICATE OF CORRECTION

PATENT NO.        : 8,565,891 B2                                    Page 1 of 1
APPLICATION NO.   : 11/921537
DATED             : October 22, 2013
INVENTOR(S)       : Mumbru et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 840 days.

Signed and Sealed this

Fifteenth Day of September, 2015

Michelle K. Lee
*Director of the United States Patent and Trademark Office*